(12) United States Patent
Rosen et al.

(10) Patent No.: US 12,414,931 B1
(45) Date of Patent: Sep. 16, 2025

(54) TREATMENT OF CANCER USING ORGANOARSENICALS

(71) Applicants: Barry P. Rosen, Boynton Beach, FL (US); Kunie Yoshinaga-Sakurai, Miami, FL (US); Venkadesh Sarkarai Nadar, Miami, FL (US)

(72) Inventors: Barry P. Rosen, Boynton Beach, FL (US); Kunie Yoshinaga-Sakurai, Miami, FL (US); Venkadesh Sarkarai Nadar, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 18/658,542

(22) Filed: May 8, 2024

(51) Int. Cl.
  *A61K 31/285*   (2006.01)
  *A61P 35/00*    (2006.01)
  *C12N 9/99*     (2006.01)
  *C12Q 1/34*     (2006.01)

(52) U.S. Cl.
  CPC ............ *A61K 31/285* (2013.01); *A61P 35/00* (2018.01); *C12N 9/99* (2013.01); *C12Q 1/34* (2013.01); *C12Y 305/01002* (2013.01)

(58) Field of Classification Search
  None
  See application file for complete search history.

(56) References Cited

U.S. PATENT DOCUMENTS

| | | | | |
|---|---|---|---|---|
| 10,934,318 B1 * | 3/2021 | Rosen | ............... | A61B 17/083 |
| 2015/0191762 A1 * | 7/2015 | Rosen | ............... | C12Q 1/689 |
| | | | | 435/252.33 |

OTHER PUBLICATIONS

Vocabulary.com [Online]. "Environment". Retrieved from the Internet: <https://www.vocabulary.com/dictionary/environment>. Accessed Oct. 29, 2024. pp. 1-2. (Year: 2024).*

Dilda et al. "Arsenical-Based Cancer Drugs". Cancer Treat Rev. Oct. 2007; 33(6):542-564. (Year: 2007).*
Soignet et al. "Complete Remission After Treatment of Acute Promyelocytic Leukemia with Arsenic Trioxide". N Engl J Med. Nov. 1998; 339(19):1341-1348. (Year: 1998).*
Howlader et al. "Chemical Synthesis of the Organoarsenical Antibiotic Arsinothricin". RSC Adv. 2021; 11:35600-35606. (Year: 2021 ).*
Suzol et al. "Semisynthesis of the Organoarsenical Antibiotic Arsinothricin". Journal of Natural Products. Aug. 24, 2020; 83(9): 2809-2813. (Year: 2020).*
Nguyen et al. "Alone and Together: Current Approaches to Targeting Glutaminase Enzymes as Part of Anti-Cancer Therapies". Future Drug Discovery. 2022; 4(4), FDD79. (Year: 2022).*
Don et al. "A Peptide Trivalent Arsenical Inhibits Tumor Angiogenesis by Perturbing Mitochondrial Function in Angiogenic Endothelial Cells". Cancer Cell. May 2003; 3(5):497-509. (Year: 2003).*
Rajaram et al. "Targeting Mutant p53 with Arsenic Trioxide: A Preclinical Study Focusing on Triple Negative Breast Cancer". Translational Oncology. Aug. 2024; 46:102025. (Year: 2024).*
Pang et al. "Tumor-Promoting and Pro-Angiogenic Effects of Roxarsone via VEGFR2/PLCGamma/PKC Signaling". Chemico-Biological Interactions; Aug. 2, 20185; 292:110-120. (Year: 2018).*

* cited by examiner

*Primary Examiner* — Leslie A. Royds Draper
(74) *Attorney, Agent, or Firm* — SALIWANCHIK, LLOYD & EISENSCHENK

(57) ABSTRACT

The subject invention provides organoarsenicals or salts thereof, compositions comprising an organoarsenical or a salt thereof, and methods of using the organoarsenicals or salts thereof, or compositions for inhibiting glutaminase and for treating cancers. Specifically, the subject invention provides methods of inhibiting glutaminase (e.g., KGA) catalytic activity in a cell, methods of treating cancer or a tumor via, for example, the inhibition of glutaminase activity, and methods of disrupting and/or inhibiting growth and proliferation of cancerous or tumorous cells.

9 Claims, 12 Drawing Sheets
(2 of 12 Drawing Sheet(s) Filed in Color)

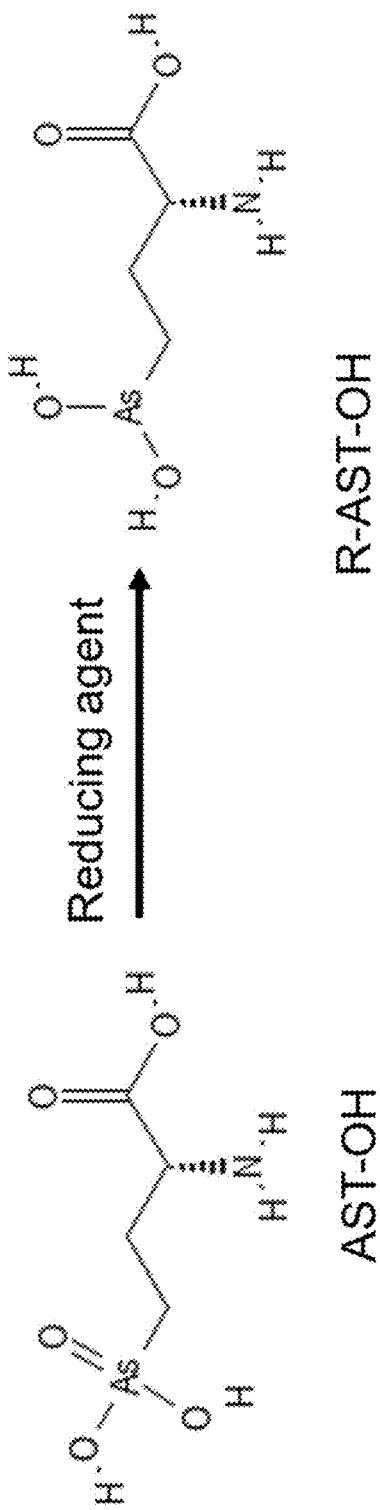
FIG. 3
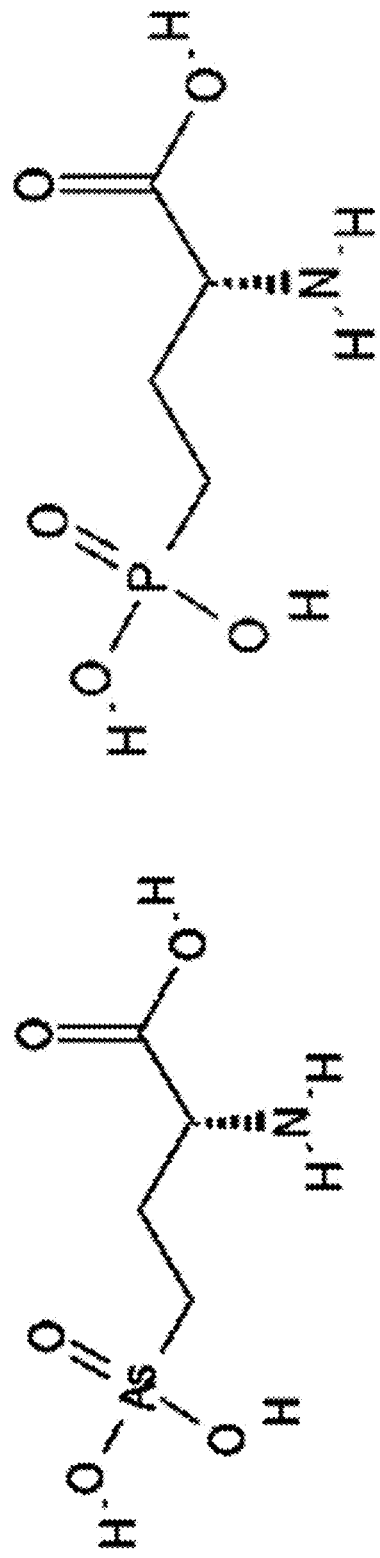
FIG. 4A
FIG. 4B

TREATMENT OF CANCER USING ORGANOARSENICALS

GOVERNMENT SUPPORT

The subject invention was made with government support under a research project supported by the National Institutes of Health grant number R35GM136211. The government has certain rights in the invention.

BACKGROUND OF INVENTION

Cancer is the second-leading cause of death in the United States, behind only heart disease. Breast cancer is the second-leading cause of death for women. Breast cancer has historically been subclassified by three molecular markers: estrogen receptors (ER), progesterone receptors (PR) and human epidermal growth factor receptor 2 (EGFR2/Her2), all of which contribute to the prognosis and choice of treatment. Breast cancers that are ER/PR positive are candidates for endocrine therapy, and Her2 positive breast cancers can be treated with anti-Her2 drugs such as Herceptin®. Breast cancer that is ER/PR/Her2 negative (or triple-negative breast cancer (TNBC)) is the most aggressive form. Compared to other types of breast cancer, TNBC lacks targeted therapies and has a poorer prognosis. Ten to twenty percent of breast cancers are TNBC, which spread beyond the breast and recur after treatments. Breast cancer diagnosis and treatment have improved significantly over the years, but TNBC remains a challenge due to aggressive progression and lack of targeted therapies.

Cancer cells have the ability to utilize glutamine as an energy source for rapid growth and proliferation. In addition, glutamine is used in many intracellular processes in cancer cells, including biosynthesis of proteins, lipids, nucleic acids and generation of ATP. Conversion of glutamine to glutamate by the mitochondrial enzyme glutaminase (GLS) is the first step in intracellular utilization (FIG. 1), and expression of glutaminase has been shown to be related to TNBC.

Therapeutic approaches to TNBC have been developed using GLS inhibitors. There are two forms of GLS in human cells: glutaminase C (GAC) and kidney-type glutaminase (KGA). Oncogenes such as c-Myc, Raf, Ras and Rho GTPases upregulate KGA expression in cancer cells, especially TNBC cells. For example, the glutamate analog DON (6-diazo-5-oxo-L-norlucine) inhibits glutaminase by attacking the side chain of Ser286 with a nucleophile. As a result of catalysis, the diazo (N2) group of DON is released, leaving 5-oxo-1-norleucine (ON) covalently bound to Ser286, inhibiting glutaminase activity. Inhibition by DON is significantly better than other glutamate analogues. However, DON's toxicity prevents it from progressing to clinical trials.

The small molecule inhibitors BPTES (bis-2-(5-phenylacetamido-1,2,4-thiadiazol-2-yl) ethyl sulfide) and CB-968 inhibit KGA by binding to an allosteric site. Because of its poor solubility and bioavailability, BPTES is not a candidate for TNBC treatment. CB-968 is currently in Phase-1 clinical trials for TNBC because of its selective inhibition of glutaminase. However, not all TNBCs respond to CP-968 due to resistance (FIG. 2). These current KGA inhibitors are not clinically effective and new glutaminase inhibitors are urgently needed.

Over the last few centuries, metals such as platinum, gold and metalloids, including arsenic- and boron-based compounds, have been developed as anti-cancer drugs. Since 1865, Fowler's solution, which contains sodium arsenite as its active ingredient, was used to treat cancer and other diseases. In 1910, Paul Ehrlich introduced the organoarsenical salvarsan to treat syphilis and trypanosomiasis. In the modern era, arsenic trioxide (Trisenox) has been approved by the U.S. Federal Drug Administration as a chemotherapeutic drug for treatment of acute promyelocytic leukemia. An advantage of trivalent arsenicals is that they easily form a covalent bond with the thiol group of cysteine residues in proteins and act as a covalent warhead.

Arsinothricin (2-amino-4-(hydroxymethylarsinoyl) butanoate (AST)) is a pentavalent organoarsenical and non-proteinogenic amino acid analog of glutamine that is a potent inhibitor of glutamine synthetase. AST is an effective broad-spectrum antibiotic against both Gram-positive and Gram-negative bacteria. In addition, the pentavalent organoarsenical roxarsone (3-nitro-4-hydroxyphenylarsonic acid (Rox(V)) has been widely used in animal husbandry as an antimicrobial growth promoter.

Thus, there is a need to identify organoarsenicals for use in glutaminase inhibition. There is also a need for developing new strategies for treating glutaminase related diseases such as cancer.

BRIEF SUMMARY OF INVENTION

The subject invention provides compounds as glutaminase inhibitors, compositions and methods for inhibiting glutaminase and treating diseases or conditions via, for example, the inhibition of glutaminase by using compounds or compositions of the subject invention.

In one embodiment, the subject invention provides compounds of organoarsenicals for use as glutaminase (e.g., KGA) inhibitors. In specific embodiments, the organoarsenicals are selected from, for example, trivalent organoarsenicals, pentavalent organoarsenicals and salts thereof.

In one embodiment, the subject invention also provides a composition comprising an organoarsenical of the subject invention. In one embodiment, the subject invention provides a pharmaceutical composition comprising a trivalent organoarsenical and/or a pentavalent organoarsenical of the subject invention or a salt thereof for inhibiting glutaminase and for treating any disease that is correlated with expression and/or catalytic activity of glutaminase, e.g., KGA.

In one embodiment, the subject invention provides methods and strategies for inhibiting glutaminase (e.g., KGA) and for treating any disease that is correlated with expression and/or catalytic activity of glutaminase, e.g., KGA.

In one embodiment, the subject invention provides a method of inhibiting glutaminase (e.g., KGA) catalytic activity in a cell, the method comprising contacting the cell with a trivalent organoarsenical, a pentavalent organoarsenical, and/or a salt thereof; or contacting the cell with a composition comprising a trivalent organoarsenical, a pentavalent organoarsenical, and/or a salt thereof.

In specific embodiments, the glutaminase (e.g., KGA) catalytic activity is inhibited by forming one or more covalent bonds between the glutaminase (e.g., KGA) and the trivalent organoarsenical, the pentavalent organoarsenical, and/or a salt thereof, wherein at least one of the covalent bonds is an As—S bond. In a specific embodiment, the trivalent organoarsenical is at least one of the trivalent form of hydroxyarsinothricin (R-AST-OH) and the trivalent form of roxarsone. In a specific embodiment, the pentavalent organoarsenical is at least one of the thiolated hydroxyarsinothricin (T-AST-OH) and the dithiolated hydroxyarsinothricin (DT-AST-OH).

In specific embodiments, the cell is a cancer cell, preferably, a triple-negative breast cancer (TNBC) cell.

In another embodiment, the subject invention provides a method of treating cancer or a tumor in a subject, the method comprising administering to the subject an effective amount of a trivalent organoarsenical, a pentavalent organoarsenical, and/or a salt thereof, or an effective amount of a composition comprising a trivalent organoarsenical, a pentavalent organoarsenical, and/or a salt thereof. In specific embodiments, the administration may be selected from, for example, local, oral, nasal, topical, intratumoural, transdermal, intra-articular, intravenous, intraperitoneal, intradermal, subcutaneous, and intramuscular routes.

In specific embodiments, the method of treating cancer or a tumor further comprises evaluating the activity of glutaminase, e.g., KGA of the subject. In specific embodiments, the method of treating cancer or a tumor further comprises forming at least one covalent bond between the glutaminase, e.g., KGA and the trivalent organoarsenical, the pentavalent organoarsenical, and/or a salt thereof, wherein the at least one of the covalent bond is an As—S bond. In a specific embodiment, the cancer is TNBC.

In one embodiment, the subject invention provides a method of disrupting and/or inhibiting growth and/or proliferation of cancerous or tumorous cells, the method comprising introducing into an environment in which the cancerous or tumorous cells exist, an effective amount of a trivalent organoarsenical, a pentavalent organoarsenical, and/or a salt thereof, or a pharmaceutical composition comprising a trivalent organoarsenical, a pentavalent organoarsenical, and/or a salt thereof.

In a specific embodiment, the trivalent organoarsenical is at least one of the trivalent form of hydroxyarsinothricin and the trivalent form of roxarsone.

In specific embodiments, the method of disrupting and/or inhibiting growth and proliferation of cancerous or tumorous cells further comprises detecting the activity of glutaminase, e.g., KGA. In specific embodiments, the method of disrupting and/or inhibiting growth and proliferation of cancerous or tumorous cells further comprises forming one or more covalent bonds between the glutaminase, e.g., KGA and the organoarsenical including the trivalent organoarsenical, the pentavalent organoarsenical, and/or a salt thereof, wherein at least one of the covalent bonds is an As—S bond.

In specific embodiments, the method of disrupting and/or inhibiting growth and proliferation of cancerous or tumorous cells is selective in disrupting and/or inhibiting the growth and proliferation of cancerous or tumorous cells over healthy cells.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 3. Preparation of trivalent R-AST-OH by chemical reduction of pentavalent AST-OH.

FIGS. 4A-4E. Chemical structures: (4A) hydroxyarsinothricin (AST-OH); (4B) 2-amino-4-phosphonobutyric acid (AP4); (4C) 6-diazo-5-oxo-L-norleucine (DON); (4D) trivalent hydroxyarsinothricn (R-AST-OH); and (4E) trivalent roxarsone (Rox(III)).

DETAILED DESCRIPTION OF INVENTION

Figure 1:
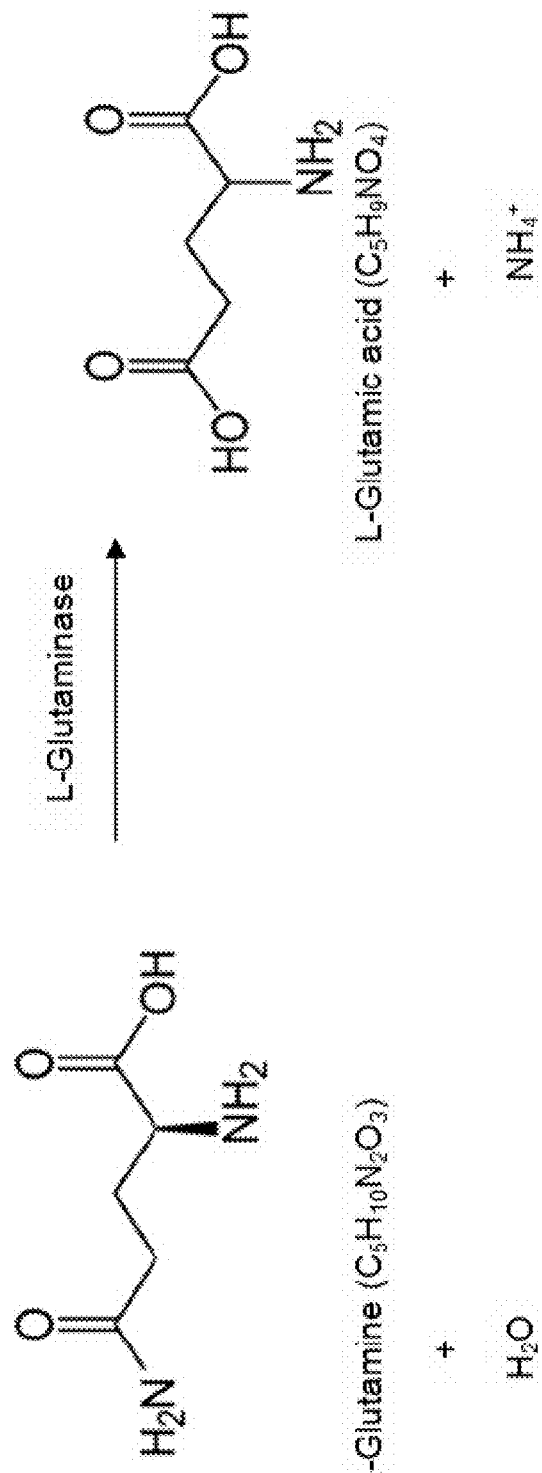
FIG. 1. Conversion of glutamine to glutamate by the mitochondrial enzyme glutaminase (GLS).
Figure 2:
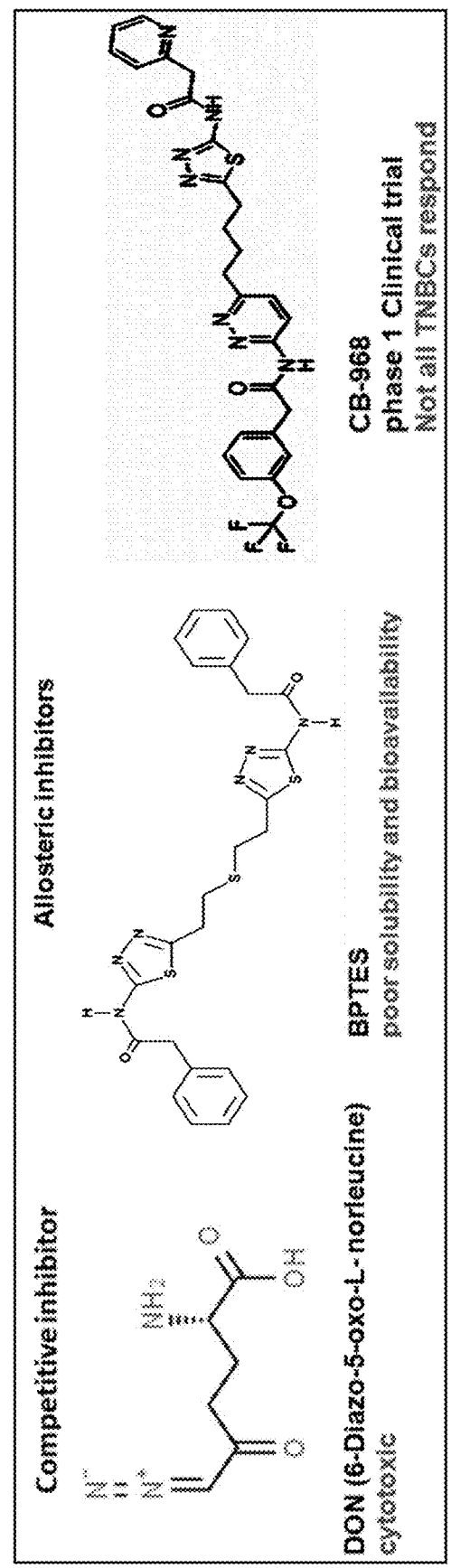
FIG. 2. Current KGA inhibitors and drawbacks thereof.

The subject invention provides compounds of organoarsenicals for use as glutaminase (e.g., KGA) inhibitors, and pharmaceutical compositions and formulations comprising an organoarsenical for treating any disease that is correlated with expression and/or catalytic activity of glutaminase, e.g., KGA.

In one embodiment, the organoarsenical is selected from, for example, trivalent organoarsenicals, pentavalent organoarsenicals and salts thereof.

The subject invention also provides methods of using the organoarsenical for inhibiting glutaminase (e.g., KGA) activity, and for treating any disease that is correlated with expression and/or activity of glutaminase, e.g., KGA.

As used herein, reference to "any disease that is correlated with expression and/or activity of glutaminase" refers to any disease whose occurrence or progression is initiated, promoted, and/or aggravated by expression and/or activity of glutaminase, e.g., KGA.

In one embodiment, the disease that is correlated with expression and/or activity of glutaminase, e.g., KGA, according to the subject invention may be any disease with inhibiting glutaminase, e.g., KGA, as a potential therapeutic target, such disease includes, but is not limited to, age-related diseases (such as age-related organ dysfunction, atherosclerosis, type 2 diabetes, fatigue, hair graying, sarcopenia, adiposity, neurogenesis, fibrosis and glaucoma), CNS disorders, neurodegenerative diseases, and cancers. In specific embodiments, the disease that is correlated with expression and/or activity of glutaminase, e.g., KGA, according to the subject invention is cancer, preferably, breast cancer, more preferably, TNBC.

The compounds, compositions, formulations and methods of use provided by the subject invention are described with further details in the following embodiments.

Compounds

According to the subject invention, compounds of organoarsenicals are provided as glutaminase (e.g., KGA) inhibitors for treating any disease that is correlated with expression and/or activity of glutaminase, e.g., KGA.

In one embodiment, the organoarsenicals are selected from, for example, trivalent organoarsenicals, pentavalent organoarsenicals and salts thereof. In a specific embodiment, the pentavalent organoarsenicals are selected from, for example, thiolated, dithiolated and trithiolated pentavalent organoarsenicals.

In one embodiment, trivalent organoarsenicals of the subject invention are prepared by reducing pentavalent organoarsenicals such as AST-OH.

As used herein, the term "trivalent organoarsenical" refers to an organoarsenical with at least one arsenic atom being in a trivalent form, i.e., with a valency of three, which can form three bonds. As used herein, the term "pentavalent organoarsenical" refers to an organoarsenical with at least one arsenic atom being in a pentavalent form, i.e., with a valency of five, which can form five bonds.

In one embodiment, the trivalent organoarsenticals comprise a trivalent arsenic atom forming three covalent bonds selected from, for example, As—C, As—N, As—O, AS—OH and As—S bonds. In specific embodiments, the trivalent organoarsentical comprises a trivalent arsenic atom forming two As—OH bonds and one As—C bond. In a specific embodiment, the C of the As—C bond is in an alkyl chain or a 5 or 6 membered ring (e.g., aryl or substituted aryl).

In one embodiment, the trivalent organoarsenicals have similar chemical structures to that of the amino acid glutamine. In one embodiment, the trivalent organoarsenicals comprise an arsenical moiety and a moiety comprising at least one of carboxylate group and nitro group. In one embodiment, the arsenical moiety of the trivalent organoarsenicals comprises at least one arsenic atom being in trivalent form.

In one embodiment, the trivalent organoarsenicals are selected from, for example, trivalent hydroxyarsinothricin (R-AST-OH), trivalent roxarsone (Rox(III)), and a salt thereof. In one embodiment, the R-AST-OH is in L-form, R-form, or a racemic mixture thereof.

In one embodiment, the pentavalent organoarsenicals of the subject invention have a general structure of formula (I):

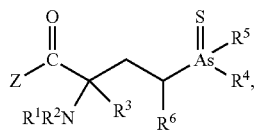

(I)

wherein Z is $OR^7$, $NHR^8$, $NR^8R^9$ or $NHCHR^{10}R^{11}$; $R^1$, $R^2$, $R^3$, $R^4$, $R^5$, $R^6$, $R^7$, $R^8$, $R^9$, $R^{10}$, and $R^{11}$ are independently selected from, for example, hydrogen, alkyl, substituted alkyl, aryl, substituted aryl, benzyl, substituted benzyl, benzoyl, substituted benzoyl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, alkoxy, substituted alkoxy, acyl, sulfhydryl, halogen, amino, substituted amino, hydroxyl, hydroxylalkyl, substituted hydroxylalkyl, —C(O) $R^{12}$, —COOR$^{13}$, and —OR$^{14}$, wherein $R^{12}$, $R^{13}$ and $R^{14}$ are independently selected from, for example, hydrogen, alkyl, substituted alkyl, aryl, substituted aryl, benzyl, substituted benzyl, benzoyl, substituted benzoyl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, alkoxy, substituted alkoxy, acyl, sulfhydryl, halogen, amino, substituted amino, hydroxyl, hydroxylalkyl, and substituted hydroxylalkyl.

In one embodiment, Z is $OR^7$ or $NHCHR^{10}R^{11}$; $R^1$ and $R^2$ are independently selected from hydrogen, alkyl, substituted alkyl, aryl, substituted aryl, acetyl, benzyl, and benzoyl; $R^3$ is hydrogen or alkyl; $R^4$ is OH, alkyl, substituted alkyl, aryl, substituted aryl, heteroalkyl, substituted heteroalkyl, acetyl, benzyl, benzoyl or sulfhydryl; $R^5$ is OH, alkyl, substituted alkyl, aryl, substituted aryl, heteroalkyl, substituted heteroalkyl, acetyl, benzyl, benzoyl or sulfhydryl; $R^6$ is hydrogen, or alkyl; $R^7$ is hydrogen, alkyl, substituted alkyl, aryl, substituted aryl, benzyl, benzoyl, heteroalkyl, or substituted heteroalkyl; $R^{10}$ is hydrogen, alkyl, or substituted alkyl; and $R^{11}$ is hydrogen, alkyl, substituted alkyl, aryl, substituted aryl, heteroalkyl, substituted heteroalkyl, alkoxy, amino, or substituted amino.

In one embodiment, Z is $OR^7$; $R^1$ and $R^2$ are independently selected from hydrogen, alkyl, and substituted alkyl; $R^3$ is hydrogen; $R^4$ is OH, alkyl, substituted alkyl, or sulfhydryl; $R^5$ is OH, alkyl, substituted alkyl, or sulfhydryl; $R^6$ is hydrogen; $R^7$ is hydrogen, alkyl, or substituted alkyl; $R^{10}$ is hydrogen, alkyl, or substituted alkyl; and $R^{11}$ is hydrogen, alkyl, substituted alkyl, amino, or substituted amino.

In a specific embodiment, the pentavalent organoarsenicals are selected from thiolated T-AST-OH having a structure of

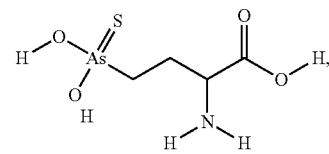

dithiolated DT-AST-OH having a structure of

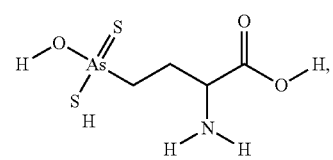

and a salt thereof.

In one embodiment, the T-AST-OH or DT-AST-OH is in L-form, R-form, or racemic mixture thereof.

In specific embodiments, catalytic activity of the glutaminase, e.g., KGA, is inhibited by the trivalent organoarsenicals via forming at least one covalent bond between the glutaminase, e.g., KGA, and the trivalent organoarsenicals.

In certain embodiments, the arsenical moiety of the trivalent organoarsenical forms at least one covalent bond with catalytic site of the glutaminase, e.g., KGA. In a specific embodiment, at least one trivalent form arsenic atom within the trivalent organoarsenical forms at least one covalent bond with a catalytic site of the KGA. In certain embodiments, the carboxylate group of the trivalent organoarsenical forms at least one covalent bond with a catalytic site of the KGA. In certain embodiments, the nitro group of the trivalent organoarsenical forms at least one covalent bond with a catalytic site of the KGA.

In one embodiment, the at least one covalent bond formed between the glutaminase, e.g., KGA, and the trivalent organoarsenicals may be selected from, for example, As—C, As—N, As—O, As—S, C—C, C—N, C—O, C—S, N—N, N—O, and N—S bonds.

In specific embodiments, catalytic activity of the glutaminase, e.g., KGA is inhibited by the pentavalent organoarsenicals via forming at least one covalent bond between the glutaminase, e.g., KGA, and the pentavalent organoarsenicals. In one embodiment, the at least one covalent bond formed between the glutaminase, e.g., KGA, and the pentavalent organoarsenicals may be selected from, for example, As—C, As—N, As—O, As—S, C—C, C—N, C—O, C—S, N—N, N—O, and N—S bonds.

As used herein, references to "catalytic activity" or "activity" of glutaminase, e.g., KGA, refers to the ability of glutaminase, e.g., KGA, to convert glutamine to glutamate.

As used herein, references to "catalytic site" of glutaminase, e.g., KGA refers to glutamine binding site of glutaminase, e.g., KGA.

In certain embodiments, the trivalent organoarsenicals or the pentavalent organoarsenicals of the subject invention can be formulated into pharmaceutically acceptable salt forms. Pharmaceutically acceptable salt forms include, for example, the acid addition salts and include hydrochloric, hydrobromic, nitric, phosphoric, carbonic, sulphuric, and organic acids like acetic, propionic, benzoic, succinic, fumaric, mandelic, oxalic, citric, tartaric, maleic, and the like. Pharmaceutically acceptable base addition salts include, for example, sodium, potassium, calcium, ammonium, and magnesium salts. Pharmaceutically acceptable salts of the trivalent organoarsenicals or the pentavalent organoarsenicals of the invention can be prepared using conventional techniques.

Compositions and Formulations

According to the subject invention, pharmaceutical compositions and formulations comprising the organoarsenicals or salts thereof described herein are provided for inhibiting activity of glutaminase (e.g., KGA), and for treating any disease that is correlated with expression and/or activity of glutaminase, e.g., KGA.

In one embodiment, the pharmaceutical composition of the subject invention comprises a therapeutically-effective amount of an organoarsenical of the subject invention or a salt thereof.

In one embodiment, the pharmaceutical composition of the subject invention may optionally further comprise one or more therapeutic agents. The therapeutic agent may comprise, for example, a chemotherapeutic agent, immunotherapeutic agent or interferon (IFN)), gene therapy and/or radio therapeutic agent. The therapeutic agent may further comprise other cytotoxic agents such as anti-tumour peptides, cytokines and growth factors, and/or cancer vaccines.

As used herein, the term "effective amount" or "therapeutically-effective amount" refers to that amount of organoarsenicals or salts thereof, optionally, in combination with one or more therapeutic agents, described herein that is sufficient to effect inhibition of activity of glutaminase, e.g., KGA, and/or to effect treatment of the disease that is correlated with expression and/or activity of glutaminase, e.g., KGA. The therapeutically-effective amount may vary depending upon the intended application, the subject, and the disease being treated, e.g., the weight and age of the subject, the severity of the disease, the manner of administration and the like, which can readily be determined by one of ordinary skill in the art. The specific dose will vary depending on, for example, the particular dosing regimen to be followed, whether it is administered in combination with other compounds, timing of administration, the tissue to which it is administered, and the physical delivery system in which it is carried.

In one embodiment, the pharmaceutical composition of the subject invention also comprises a pharmaceutically-acceptable carrier. "Pharmaceutically-acceptable carrier" refers to a diluent, adjuvant or excipient with which the organoarsenicals disclosed herein can be formulated. Typically, a "pharmaceutically-acceptable carrier" is a substance that is non-toxic, biologically tolerable, and otherwise biologically suitable for administration to a subject, such as an inert substance, added to a pharmacological composition or otherwise used as a diluent, adjuvant or excipient to facilitate administration of the composition disclosed herein and that is compatible therewith. Examples of carriers suitable for use in the pharmaceutical compositions are known in the art and such embodiments are within the purview of the invention.

In one embodiment, the organoarsenicals or salts thereof of the subject invention can be formulated according to known methods for preparing pharmaceutically useful formulations. In general, the organoarsenicals or salts thereof of the subject invention can be formulated such that an effective amount of the organoarsenicals is combined with a suitable carrier in order to facilitate effective administration of the organoarsenicals. The formulations of the subject invention can be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application.

The carrier and/or diluent can generally be any suitable medium by which the desired purpose is achieved. Particularly, the carrier and/or diluent should not deteriorate the pharmacological potency of the organoarsenicals and the capability of the organoarsenicals to be directed to a desired target within, or on, the subject body. Preferably, said carrier and/or diluent is/are selected from water, physiologically acceptable aqueous solutions containing salts and/or buffers and any other solution acceptable for administration to a subject.

Carriers and/or excipients according the subject invention can include solvents, diluents, buffers (such as, e.g., neutral buffered saline, phosphate buffered saline, or optionally Tris-HCl, acetate or phosphate buffers), oil-in-water or water-in-oil emulsions, aqueous compositions with or without inclusion of organic co-solvents suitable for, e.g., IV use, solubilizers (e.g., Polysorbate 65, Polysorbate 80), colloids, dispersion media, vehicles, fillers, chelating agents (e.g., EDTA or glutathione), amino acids (e.g., glycine), proteins, disintegrants, binders, lubricants, wetting agents, emulsifiers, sweeteners, colorants, flavorings, aromatizers, thickeners (e.g. carbomer, gelatin, or sodium alginate), coatings, preservatives (e.g., Thimerosal, benzyl alcohol, polyquaterium), antioxidants (e.g., ascorbic acid, sodium metabisulfite), tonicity controlling agents, absorption delaying agents, adjuvants, bulking agents (e.g., lactose, mannitol) and the like. The use of carriers and/or excipients in the field of drugs and supplements is well known. Except for any conventional media or agent that is incompatible with the organoarsenicals or with the salts thereof, carrier or excipient use in the subject formulations may be contemplated.

In certain embodiments, the formulations can be administered for treatment through one or more of several delivery methods. Methods of oral drug delivery include, for example, tablets, capsules, sachets, powders, pellets, granules, granulates, mixtures, syrups, solutions, suspensions, or emulsions. Methods of intravenous, intramuscular, intraarticular, or subcutaneous injection include, for example, solution, suspension, or emulsion. Methods of topical treatment include, for example, lotions, creams, gels, pastes, ointments, transdermal patches, powders, foams, tinctures, oils, or sprays.

In one embodiment, the organoarsenicals or salts thereof are formulated as an orally consumable product, such as, for example a food item, capsule, pill, or drinkable liquid. An orally deliverable pharmaceutical is any physiologically active substance delivered via initial absorption in the gastrointestinal tract or into the mucus membranes of the mouth. The organoarsenicals or salts thereof can also be formulated as a solution that can be administered via, for example, injection, which includes intravenously, intraperitoneally, intramuscularly, intrathecally, or subcutaneously.

Orally consumable products according to the subject invention are any preparations or compositions suitable, e.g., for consumption, or for nutrition, and are products intended to be introduced into the human or animal oral cavity, to remain there for a certain period of time, and then either be swallowed (e.g., food ready for consumption or pills) or to be removed from the oral cavity. While an orally-deliverable pharmaceutical can be formulated into an orally consumable product, and an orally consumable product can comprise an orally deliverable pharmaceutical.

Orally consumable products include all substances or products intended to be ingested by humans or animals in a processed, semi-processed, or unprocessed state. This also includes substances that are added to orally consumable products (particularly food and pharmaceutical products) during their production, treatment, or processing and intended to be introduced into the human or animal oral cavity.

Orally consumable products can also include substances intended to be swallowed by humans or animals and then digested in an unmodified, prepared, or processed state; the orally consumable products according to the invention therefore also include casings, coatings, or other encapsulations that are intended to be swallowed together with the product or for which swallowing is to be anticipated.

In one embodiment, the orally consumable product is a capsule, pill, syrup, emulsion, or liquid suspension containing a desired orally deliverable substance. In one embodiment, the orally consumable product can comprise an orally deliverable substance in powder form, which can be mixed with water or another liquid to produce a drinkable orally consumable product.

In one embodiment, the organoarsenicals or salts thereof of the subject invention can be formulated into preparations, for example, solid, semi-solid, liquid, or gaseous forms, such as tablets, capsules, powders, granules, ointments, solutions, suppositories, injections, inhalants, and aerosols.

In certain embodiments, the formulation is in a powder form. The pharmaceutically-acceptable carrier is a finely divided solid that is in a mixture with the finely divided active compounds, i.e., the organoarsenicals or salts thereof. In another embodiment, the formulation is in a tablet form. The active component is mixed with the pharmaceutically-acceptable carrier having the necessary binding capacity in suitable proportions and compacted in desired shape and size. Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

In one embodiment, the organoarsenicals or salts thereof of the subject invention can be made into aerosol formulations so that, for example, it can be nebulized or inhaled. Suitable pharmaceutical formulations for administration in the form of aerosols or sprays are, for example, powders, particles, solutions, suspensions, or emulsions. Formulations for oral or nasal aerosol or inhalation administration may also be formulated with carriers, including, for example, saline, polyethylene glycol or glycols, DPPC, methylcellulose, or in mixture with powdered dispersing agents or fluorocarbons. Aerosol formulations can be placed into pressurized propellants, such as dichlorodifluoromethane, propane, nitrogen, fluorocarbons, and/or other solubilizing or dispersing agents known in the art. Illustratively, delivery may be by use of a single-use delivery device, a mist nebulizer, a breath-activated powder inhaler, an aerosol metered-dose inhaler (MDI), or any other of the numerous nebulizer delivery devices available in the art. Additionally, mist tents or direct administration through endotracheal tubes may also be used.

In one embodiment, the organoarsenicals or salts thereof of the subject invention can be formulated for administration via topical application onto the skin, for example, as topical compositions, which include rinse, spray, or drop, lotion, gel, ointment, cream, foam, powder, solid, sponge, tape, vapor, paste, tincture, or using a transdermal patch. Suitable formulations of topical applications can comprise in addition to any of the pharmaceutically active carriers, for example, emollients such as carnauba wax, cetyl alcohol, cetyl ester wax, emulsifying wax, hydrous lanolin, lanolin, lanolin alcohols, microcrystalline wax, paraffin, petrolatum, polyethylene glycol, stearic acid, stearyl alcohol, white beeswax, or yellow beeswax. Additionally, the compositions may contain humectants such as glycerin, propylene glycol, polyethylene glycol, sorbitol solution, and 1,2,6 hexanetriol or permeation enhancers such as ethanol, isopropyl alcohol, or oleic acid.

In one embodiment, the effective amount of the organoarsenicals or salts thereof can be administered through, for example, oral, rectal, bronchial, nasal, topical, buccal, sublingual, transdermal, vaginal, intramuscular, intraperitoneal, intravenous, intra-arterial, intracerebral, interaocular administration or in a form suitable for administration by inhalation or insufflation, including powders and liquid aerosol administration, or by sustained release systems such as semipermeable matrices of solid hydrophobic polymers containing the compound(s) of the invention. Administration may be also by way of other carriers or vehicles such as micelles, liposomes, vesicles, implants (e.g., microimplants), synthetic polymers, microspheres, nanoparticles, and the like.

In one embodiment, the organoarsenicals or salts thereof of the subject invention can be formulated for administration via injection, for example, as a solution or suspension. The solution or suspension can comprise suitable non-toxic, parenterally-acceptable diluents or solvents, such as mannitol, 1,3-butanediol, water, Ringer's solution, or isotonic sodium chloride solution, or suitable dispersing or wetting and suspending agents, such as sterile, non-irritant, fixed oils, including synthetic mono- or diglycerides, and fatty acids, including oleic acid. One illustrative example of a carrier for intravenous use includes a mixture of 10% USP ethanol, 40% USP propylene glycol or polyethylene glycol 600 and the balance USP Water for Injection (WFI). Other illustrative carriers for intravenous use include 10% USP ethanol and USP WFI; 0.01-0.1% triethanolamine in USP WFI; or 0.01-0.2% dipalmitoyl diphosphatidylcholine in USP WFI; and 1-10% squalene or parenteral vegetable oil-in-water emulsion. Water or saline solutions and aqueous dextrose and glycerol solutions may be preferably employed as carriers, particularly for injectable solutions. Illustrative examples of carriers for subcutaneous or intramuscular use include phosphate buffered saline (PBS) solution, 5% dextrose in WFI and 0.01-0.1% triethanolamine in 5% dextrose or 0.9% sodium chloride in USP WFI, or a 1 to 2 or 1 to 4 mixture of 10% USP ethanol, 40% propylene glycol and the balance an acceptable isotonic solution such as 5% dextrose or 0.9% sodium chloride; or 0.01-0.2% dipalmitoyl diphosphatidylcholine in USP WFI and 1 to 10% squalene or parenteral vegetable oil-in-water emulsions.

In one embodiment, the organoarsenicals or salts thereof of the subject invention can be formulated for parenteral administration (e.g., by injection). In addition, the organoarsenicals or salts thereof may be presented in unit dose form in ampoules, pre-filled syringes, and small volume infusion or in multi-dose containers with or without an added preservative. The organoarsenicals or salts thereof may be in forms of suspensions, solutions, or emulsions in oily or aqueous vehicles. The organoarsenicals or salts thereof may further contain formulation agents such as suspending, stabilizing and/or dispersing agents.

In one embodiment, the organoarsenicals or salts thereof of the subject invention can be applied directly to the nasal cavity by conventional means, for example with a dropper, pipette or spray. The compositions may be provided in single or multi-dose form. Administration to the respiratory tract may also be achieved by means of an aerosol formulation in which the organoarsenicals or salts thereof are provided in a pressurized pack with a suitable propellant such as a chlorofluorocarbon (CFC) for example dichlorodifluoromethane, trichlorofluoromethane, or dichlorotetrafluoroethane, carbon dioxide, or other suitable gas.

In one embodiment, the organoarsenicals or salts thereof of the subjection invention may also be administered in a controlled release formulation such as a slow release or a fast release formulation. Such controlled release formulations of the subject invention may be prepared using methods well known to those skilled in the art. The method of administration will be determined by the attendant physician or other person skilled in the art after an evaluation of the subject's condition and requirements. In one embodiment, the organoarsenicals or salts thereof of the subject invention can also be administered utilizing liposome technology, slow release capsules, implantable pumps, and biodegradable containers. These delivery methods can, advantageously, provide a uniform dosage over an extended period of time.

In one embodiment, the pharmaceutical composition of the subject invention is provided in a unit dosage form, wherein the composition in desired form is divided into unit doses containing appropriate quantities of the organoarsenicals or salts thereof. The unit dosage form can be a packaged preparation, the package containing discrete quantities such as packaged tablets, capsules, and powders in vials or ampoules. Moreover, the unit dosage form can be a capsule, tablet, cachet, or lozenge itself, or it can be the appropriate number of any of these in packaged form. In a preferred embodiment, tablet or capsule forms are for oral administration and liquid form are for intravenous administration and continuous infusion. The quantity of the organoarsenicals in a dosage formulation that can be administered to a subject in need thereof can vary from about 1 mg to about 5000 mg, about 1 mg to about 4000 mg, about 1 mg to about 3000 mg, about 1 mg to about 2000 mg, about 1 mg to about 1500 mg, about 1 mg to about 1000 mg, about 1 mg to about 500 mg, about 5 mg to about 250 mg, or about 10 mg to about 100 mg.

Additional components which may be added to enhance the compositions and their delivery include, for example, fillers, binders, disintegrants, diluents, glidants, emulsifying agents, suspending agents, stabilizers, enhancers, flavors, dyes, pigments, pH adjusting agents, buffers, retarding agents, wetting agents, adhesion-promoting compounds, surface active agents, preservatives, antioxidant, defoamers, anti-skinning agents, texturizers, emulsifying agents, lubricants, solubility controlling agents, chelating agents, conventional carrier compositions, and mixtures thereof.

Methods of Treatment

In one embodiment, the subject invention provides novel methods and strategies for inhibiting glutaminase (e.g., KGA), and for treating any disease that is correlated with expression and/or activity of glutaminase, e.g., KGA.

In one embodiment, the subject invention provides a method of inhibiting glutaminase activity in a cell, the method comprising contacting the cell with an organoarsenical or a salt thereof of the subject invention, particularly with an effective amount of an organoarsenical or a salt thereof, or a composition comprising an organoarsenical or a salt thereof of the subject invention.

In one embodiment, the subject invention provides a method of inhibiting KGA catalytic activity in a cell, the method comprises contacting the cell with an organoarsenical or a salt thereof of the subject invention, particularly with an effective amount of an organoarsenical or a salt thereof, or a composition comprising an organoarsenical or a salt thereof of the subject invention.

In one embodiment, the method of inhibiting glutaminase (e.g., KGA) activity in a cell according to the subject invention comprises forming one or more covalent bonds between the glutaminase, e.g., KGA, and the organoarsenical or the salt thereof, as described herein in conjunction with the compounds. In one embodiment, formation of one or more covalent bonds between the glutaminase, e.g., KGA, and the organoarsenical or the salt thereof occurs upon contacting the cell with the organoarsenical or the salt thereof. In one embodiment, glutaminase (e.g., KGA) activity in the cell is inhibited by, for example, forming one or more covalent bonds between the glutaminase, e.g., KGA, and the organoarsenical or the salt thereof.

In one embodiment, the cell is obtained from a subject that has been diagnosed with a disease that is correlated with expression and/or activity of glutaminase, e.g., KGA. In one embodiment, the cell is obtained from a subject that has been diagnosed with cancer or malignant tumor. In one embodiment, the cell is obtained from a subject that has been diagnosed with breast cancer, particularly TNBC. In one embodiment, the cell is obtained from cancerous or tumorous tissues of the subject.

In one embodiment, the cell is a cancerous or tumorous cell, which is selected from, for example, prostate cancer cells, gallbladder cancer cells, intrahepatic biliary tract cancer cells, biliary tract cancer cells, oral cancer cells, pharyngeal cancer cells, laryngeal cancer cells, tongue cancer cells, duodenal cancer cells, eye tumor cells, mediastinal cancer cells, sinus cancer cells, renal pelvic cancer cells, heart cancer cells, glioblastoma cells, neuroblastoma cells, liver cancer cells, bone cancer cells, pancreatic cancer cells, skin cancer cells, head and neck cancer cells, breast cancer cells, lung cancer cells, skin or intraocular malignant melanoma cells, kidney cancer cells, uterine cancer cells, ovarian cancer cells, colon cancer cells, rectal cancer cells, anal region cancer cells, colorectal cancer cells, stomach cancer cells, testicular cancer cells, fallopian tube cancer endometrial carcinoma cells, cervical carcinoma cells, vaginal carcinoma cells, vulvar cancer cells, non-Hodgkin's lymphoma cells, esophageal cancer cells, small intestinal cancer cells, endocrine system cancer cells, thyroid cancer cells, parathyroid cancer cells, adrenal gland cancer cells, soft tissue sarcoma cells, urethral cancer cells, penile cancer cells, childhood cancer cells, lymphocytic lymphoma cells, bladder cancer cells, ureter cancer cells, renal pelvic carcinoma cells, central nervous system (CNS) cancer cells, primary CNS lymphoma cells, spinal cancer cells, brainstem glioma cells, pituitary adenoma cells, Kaposi's sarcoma cells, epidermal cancer cells, squamous cell carcinoma cells, multiple myeloma cells, B-cell lymphoma cells, Hodgkin's lymphoma cells, acute myeloid lymphoma cells, chronic myeloid leukemia cells, chronic lymphocytic leukemia cells, follicular lymphoma cells, diffuse large B-cell lymphoma cells, Burkitt's lymphoma cells, immune large-cell lymphoma cells, progenitor B-lymphoblastic lymphoma cells, mantle cell lymphoma cells, acute lymphoblastic lymphoma cells, mycosis fungoides cells, anaplastic large-cell lymphoma cells, acute myeloid leukemia cells, acute lymphoblastic leukemia cells, hepatoblastoma cells, retinoblastoma cells, peritoneal cancer cells, brain tumor cells, thymic cancer cells, T-cell lymphoma or precursor T-lymphoblastic lymphoma cells, and any combination of the above cancer cells. In a specific embodiment, the cell is a breast cancer cell. In a further embodiment, the cell is TNBC cell. In a specific embodiment, the cell is selected from MDA-MB-231, HCC1569, and HCC38.

In one embodiment, the organoarsenicals according to the subject invention are advantageously biocompatible with healthy cells. Advantageously, the organoarsenicals according to the subject invention have selective anti-cancer or anti-tumor effects on cancerous or tumorous cells. In further embodiments, the organoarsenicals according to the subject invention selectively and significantly reduce cancerous or tumorous cell viability.

In one embodiment, the method of inhibiting glutaminase (e.g., KGA) activity in a cell may be conducted in vitro or in vivo.

In one embodiment, the method of inhibiting glutaminase (e.g., KGA) activity in a cell according to the subject invention further comprises detecting the activity of glutaminase, e.g., KGA, before, during, and/or after contacting the cell with an organoarsenical or a salt thereof of the subject invention. According to the subject invention, detecting the activity of glutaminase, e.g., KGA, may be conducted by any known process in the art by determining the enzyme concentration, the glutamate concentration, and/or kinetics of glutaminase, e.g., KGA. In a specific embodiment, detecting the activity of glutaminase, e.g., KGA, is conducted by a glutaminase activity assay.

In one embodiment, the method of inhibiting KGA activity in a cell according to the subject invention further comprises detecting the activity of KGA before and after contacting the cell with an organoarsenical or a salt thereof of the subject invention.

In specific embodiments, the activity of glutaminase, e.g., KGA, after contacting the cell with an organoarsenical or a salt thereof decreases by at least 95%, at least 90%, at least 85%, at least 80%, at least 75%, at least 70%, at least 65%, at least 60%, at least 55%, at least 50%, at least 45%, at least 40%, at least 35%, at least 30%, at least 25%, at least 20%, at least 15%, or at least 10%, compared to the activity of KGA before contacting the cell with an organoarsenical or a salt thereof.

In certain embodiments, the organoarsenical or a salt thereof according to the subject invention inhibits the activity of glutaminase, e.g., KGA, at micromolar concentrations. In certain embodiments, the organoarsenical or a salt thereof according to the subject invention exhibits a half-maximal inhibitory concentration ($IC_{50}$) against glutaminase, e.g., KGA, in a range of, for example, 0.01 µM to 400 µM, 0.05 µM to 350 µM, 0.1 µM to 300 µM, 0.2 µM to 250µ, 0.3 µM to 200 µM, 0.4 µM to 150 µM, 0.5 µM to 100µ, 0.6 µM to 50 µM, 0.7 µM to 40 µM, 0.8 µM to 30 µM, 0.9 µM to 20 µM, 1 µM to 10 µM, 1.2 µM to 8 µM, 1.4 µM to 6 µM, 1.6 µM to 4 µM, 1.8 µM to 3 µM, or 1.9 µM to 2.5µ. In specific embodiments, the organoarsenical or a salt thereof according to the subject invention exhibits a half-maximal inhibitory concentration ($IC_{50}$) against glutaminase, e.g., KGA, of 2 µM.

In one embodiment, the subject invention provides a method of inhibiting glutaminase (e.g., KGA) activity, the method comprising administering to a subject in need thereof an effective amount of an organoarsenical or a salt thereof of the subject invention or a pharmaceutical composition comprising an organoarsenical or a salt thereof.

In one embodiment, the subject invention provides a method of reducing the viability of a cancerous cell or tumorous cell, the method comprising introducing into an environment in which the cell exists, an effective amount of an organoarsenical or a salt thereof according to the present invention or a composition comprising an organoarsenical or a salt thereof. In further embodiments, the organoarsenical or a salt thereof in the method according to the present invention selectively reduces the viability of cancerous cells or tumorous cells over healthy cells. In specific embodiments, an organoarsenical or a salt thereof in the method according to the present invention selectively induces apoptosis of cancerous cells or tumorous cells over healthy cells. In particular embodiments, the cancerous or tumorous cells are those causing breast cancer, including but not limited to triple-negative breast cancer (TNBC).

In one embodiment, the method of reducing the viability of a cancerous cell or tumorous cell according to the subject invention comprises forming one or more covalent bonds between glutaminase, e.g., KGA, of the cancerous cell or tumorous cell and the organoarsenical or the salt thereof, as described herein in conjunction with the compounds. In one embodiment, formation of one or more covalent bonds between glutaminase, e.g., KGA, of the cancerous cell or tumorous cell and the organoarsenical or the salt thereof occurs upon introducing into an environment in which the cell exists, an effective amount of an organoarsenical or a salt thereof. In one embodiment, viability of a cancerous cell or tumorous cell is reduced by forming one or more covalent bonds between glutaminase, e.g., KGA, of the cancerous cell or tumorous cell and the organoarsenical or the salt thereof.

In one embodiment, the method of reducing the viability of a cancerous cell or tumorous cell according to the subject invention further comprises detecting the activity of glutaminase, e.g., KGA, before, during, and/or after introducing into an environment in which the cell exists, an effective amount of an organoarsenical or a salt thereof or a composition comprising an organoarsenical or a salt thereof. According to the subject invention, detecting the activity of glutaminase, e.g., KGA, may be conducted by any known process in the art by determining the glutaminase, e.g., KGA, concentration, the glutamate concentration, and/or kinetics of glutaminase, e.g., KGA. In one embodiment, detecting the activity of glutaminase, e.g., KGA, is conducted by a glutaminase activity assay.

In one embodiment, the method of reducing the viability of a cancerous cell or tumorous cell according to the subject invention further comprises detecting the activity of KGA before and after introducing into an environment in which the cell exists, an effective amount of an organoarsenical or a salt thereof.

In specific embodiments, the activity of glutaminase, e.g., KGA, after introducing into an environment in which the cell exists, an effective amount of an organoarsenical or a salt thereof decreases by at least 95%, at least 90%, at least 85%, at least 80%, at least 75%, at least 70%, at least 65%, at least 60%, at least 55%, at least 50%, at least 45%, at least 40%, at least 35%, at least 30%, at least 25%, at least 20%, at least 15%, or at least 10%, compared to the activity of glutaminase, e.g., KGA, before introducing into an environment in which the cell exists, an effective amount of an organoarsenical or a salt thereof.

In another embodiment, the subject invention provides a method of disrupting/inhibiting the proliferation of cancerous or tumorous cells, the method comprising introducing into an environment in which the cells exist, an effective amount of an organoarsenical or a salt thereof according to the present invention or a composition of the present invention. In further embodiments, the organoarsenicals or a salt thereof in the method according to the present invention selectively disrupts/inhibits the proliferation of cancerous or tumorous cells over healthy cells.

In one embodiment, the method of disrupting/inhibiting the proliferation of cancerous or tumorous cells according to the subject invention comprises forming one or more covalent bonds between glutaminase, e.g., KGA, of the cancerous or tumorous cells and the organoarsenical or the salt thereof, as described herein in conjunction with the compounds. In one embodiment, formation of one or more covalent bonds between glutaminase, e.g., KGA, of the cancerous or tumorous cells and the organoarsenical or the salt thereof occurs upon introducing into an environment in which the cells exist, an effective amount of an organoarsenical or a salt thereof. In one embodiment, proliferation of the cancerous or tumorous cells is disrupted/inhibited by forming one or more covalent bonds between glutaminase, e.g., KGA, of the cancerous or tumorous cells and the organoarsenical or the salt thereof.

In one embodiment, the method of disrupting/inhibiting the proliferation of cancerous or tumorous cells according to the subject invention further comprises detecting the activity of glutaminase, e.g., KGA, before, during, and/or after introducing into an environment in which the cells exist, an effective amount of an organoarsenical or a salt thereof. According to the subject invention, detecting the activity of glutaminase, e.g., KGA, may be conducted by any known process in the art by determining the glutaminase, e.g., KGA, concentration, the glutamate concentration, and/or kinetics of glutaminase, e.g., KGA. In one embodiment, detecting the activity of glutaminase, e.g., KGA, is conducted by a glutaminase activity assay.

In one embodiment, the method of disrupting/inhibiting the proliferation of cancerous or tumorous cells further comprises detecting the activity of KGA before and after introducing into an environment in which the cell exists, an effective amount of an organoarsenical or a salt thereof.

In some embodiments, the activity of glutaminase, e.g., KGA, after introducing into an environment in which the cell exists, an effective amount of an organoarsenical or a salt thereof decreases by at least 95%, at least 90%, at least 85%, at least 80%, at least 75%, at least 70%, at least 65%, at least 60%, at least 55%, at least 50%, at least 45%, at least 40%, at least 35%, at least 30%, at least 25%, at least 20%, at least 15%, or at least 10%, compared to the activity of glutaminase, e.g., KGA, before introducing into an environment in which the cell exists, an effective amount of an organoarsenical or a salt thereof.

In some embodiments, the organoarsenical or a salt thereof is introduced to the environment of target cells at a concentration ranging, for example, from 0.1 µg/ml to 500 µg/ml, from 1 µg/ml to 450 µg/ml, from 1 µg/ml to 400 µg/ml, from 5 µg/ml to 400 µg/ml, from 10 µg/ml to 350 µg/ml, from 10 µg/ml to 300 µg/ml, from 25 µg/ml to 250 µg/ml, from 50 µg/ml to 200 µg/ml, from 50 µg/ml to 150 µg/ml, from 75 µg/ml to 200 µg/ml, or from 100 µg/ml to 200 µg/ml.

In certain embodiments, an organoarsenical or a salt thereof is introduced to the environment of target cells at a concentration of at least, for example, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30% or any concentration therebetween by weight of the total composition.

In certain embodiments, an organoarsenical or a salt thereof is introduced to the environment of target cells at a concentration ranging, for example, from about 0.001% to about 2.00%, from about 0.001% to about 1.00%, from about 0.001% to about 0.90%, from about 0.001% to about 0.80%, from about 0.001% to about 0.70%, from about 0.001% to about 0.60%, from about 0.001% to about 0.50%, from about 0.001% to about 0.40%, from about 0.001% to about 0.30%, from about 0.001% to about 0.20%, or from about 0.001% to about 0.10% by weight of the total composition. In some embodiments, a composition comprises an organoarsenical or a salt thereof according to the present invention at from about 0.001% to about 0.09%, from about 0.001% to about 0.08%, from about 0.001% to about 0.07%, from about 0.001% to about 0.06%, from about 0.001% to about 0.05%, from about 0.001% to about 0.04%, from about 0.001% to about 0.03%, from about 0.001% to about 0.02%, or from about 0.001% to about 0.01% by weight of the total composition.

In certain embodiments, the organoarsenical or a salt thereof according to the subject invention exhibit a half-maximal inhibitory concentration ($IC_{50}$) against cancerous or tumorous cells in a range of, for example, 0.01 µM to 1000 µM, 0.05 µM to 900 µM, 0.1 µM to 800µ, 0.2 µM to 700µ, 0.3 µM to 600µ, 0.4 µM to 500 µM, 0.5 µM to 400 µM, 0.6 µM to 300 µM, 0.7 µM to 200 µM, 0.8 µM to 100µ, 0.9 µM to 90µ, 1 µM to 80 µM, 1.2 µM to 70µ, 1.4 µM to 60 µM, 1.6 µM to 50µ, 1.8 µM to 40µ, 1.9 µM to 30µ, 2 µM to 20 µM, 2.1 µM to 18 µM, 2.2 µM to 16 µM, 2.3 µM to 14 µM, 2.4 µM to 12 µM, 2.5 µM to 10 µM, 2.6 µM to 8 µM, 2.7 µM to 7 µM, 2.8 µM to 6 µM, 2.9 µM to 5 µM, or 3 µM to 4 µM.

In one embodiment, the organoarsenical or a salt thereof according to the subject invention exhibit a half-maximal inhibitory concentration ($IC_{50}$) against healthy cells in a range of, for example, 10 µM to 1000 µM, 15 µM to 900 µM, 20 µM to 800 µM, 25 µM to 700 µM, 30 µM to 600 µM, 35 µM to 500 µM, 40 µM to 400 µM, 45 µM to 300 µM, 50 µM to 200 µM, 55 µM to 100 µM, 60 µM to 90 µM, or 65 µM to 85 µM.

In certain embodiments, selective disruption/inhibition of the proliferation of cancerous or tumorous cells over healthy cells by the organoarsenical or a salt thereof in the method according to the present invention is manifested as higher $IC_{50}$ against healthy cells than $IC_{50}$ against cancerous or tumorous cells. In further embodiments, $IC_{50}$ of the organoarsenical or a salt thereof against healthy cells is about 100-fold, 95-fold, 90-fold, 85-fold, 80-fold, 75-fold, 70-fold, 65-fold, 60-fold, 55-fold, 50-fold, 45-fold, 40-fold, 35-fold, 30-fold, 25-fold, 20-fold, 19-fold, 18-fold, 17-fold, 16-fold, 15-fold, 14-fold, 13-fold, 12-fold, 11-fold, 10-fold, 9-fold, 8-fold, 7-fold, 6-fold, 5-fold, 4-fold, 3-fold, or 2-fold, of $IC_{50}$ of the organoarsenical or a salt thereof against cancerous or tumorous cells.

In one embodiment, the cancerous or tumorous cell is obtained from subjects that have been diagnosed with cancers including, but are not limited to, prostate cancer, gallbladder cancer, intrahepatic biliary tract cancer, biliary tract cancer, oral cancer, pharyngeal cancer, laryngeal cancer, tongue cancer, duodenal cancer, eye tumor, mediastinal cancer, sinus cancer, renal pelvic cancer, heart cancer, glioblastoma, neuroblastoma, liver cancer, bone cancer, pancreatic cancer, skin cancer, head and neck cancer, breast cancer, lung cancer, skin or intraocular malignant melanoma, kidney cancer, uterine cancer, ovarian cancer, colon cancer, rectal cancer, anal region cancer, colorectal cancer, stomach cancer, testicular cancer, fallopian tube cancer endometrial carcinoma, cervical carcinoma, vaginal carcinoma, vulvar cancer, non-Hodgkin's lymphoma, esophageal cancer, small intestinal cancer, endocrine system cancer, thyroid cancer, parathyroid cancer, adrenal gland cancer, soft tissue sarcoma, urethral cancer, penile cancer, childhood cancer, lymphocytic lymphoma, bladder cancer, ureter cancer, renal pelvic carcinoma, central nervous system (CNS) cancer, primary CNS lymphoma, tumor angiogenesis, spinal cancer, brainstem glioma, pituitary adenoma, Kaposi's sarcoma, epidermal cancer, squamous cell carcinoma, multiple myeloma, B-cell lymphoma, Hodgkin's lymphoma, acute myeloid lymphoma, chronic myeloid leukemia, chronic lymphocytic leukemia, follicular lymphoma, diffuse large B-cell lymphoma, Burkitt's lymphoma, immune large-cell lymphoma, progenitor B-lymphoblastic lymphoma, mantle cell lymphoma, acute lymphoblastic lymphoma, mycosis fungoides, anaplastic large-cell lymphoma, acute myeloid leukemia, acute lymphoblastic leukemia, hepatoblastoma, retinoblastoma, peritoneal cancer, brain tumor, thymic cancer, T-cell lymphoma or precursor T-lymphoblastic lymphoma, and any combination of the above cancers. In a preferred embodiment, the cell is a breast cancer cell. In a specific embodiment, the cell is TNBC cell. In a specific embodiment, the cell is selected from MDA-MB-231, HCC1569, and HCC38.

In one embodiment, the healthy cell is obtained from any healthy tissues of subjects without cancerous or tumorous lesions. In a specific embodiment, the healthy cell is non-tumorigenic human breast epithelial cells MCF12A.

In one embodiment, the subject invention provides a method of treating cancer or a tumor in a subject in need thereof. In one embodiment, the method of treating cancer or a tumor in a subject in need thereof according to the subject invention comprises administering to the subject an effective amount of an organoarsenical or a salt thereof or a pharmaceutical composition comprising an organoarsenical or a salt thereof.

In one embodiment, the method of treating cancer or a tumor according to the subject invention comprises forming one or more covalent bonds between glutaminase, e.g., KGA, of cancerous or tumorous cells of the subject and the organoarsenical or the salt thereof, as described herein in conjunction with the compounds. In one embodiment, formation of one or more covalent bonds between glutaminase, e.g., KGA of the cancerous or tumorous cells of the subject and the organoarsenical or the salt thereof occurs upon administering to the subject an effective amount of the organoarsenical or the salt thereof or a pharmaceutical composition comprising the organoarsenical or the salt thereof.

In one embodiment, cancer or tumor in the subject is effectively treated by forming one or more covalent bonds between glutaminase, e.g., KGA, of the cancerous or tumorous cells of the subject and the organoarsenical or the salt thereof. Effective treatments of cancer or tumor in the subject include but are not limited to, cancerous or tumorous tissues decrease or disappear, and/or cancerous or tumorous symptoms are alleviated or eliminated within the subject.

Tumors as used herein are a swelling part of the body, caused by an abnormal growth of tissue, whether benign (non-cancerous), premalignant, or malignant (cancerous). Thus, tumors may overlap with cancers. In some embodiments, tumors being treated according to the subject invention are malignant. In some embodiments, tumors being treated according to the subject invention are premalignant.

Cancers as used herein may include, but are not limited to, prostate cancer, gallbladder cancer, intrahepatic biliary tract cancer, biliary tract cancer, oral cancer, pharyngeal cancer, laryngeal cancer, tongue cancer, duodenal cancer, eye tumor, mediastinal cancer, sinus cancer, renal pelvic cancer, heart cancer, glioblastoma, neuroblastoma, liver cancer, bone cancer, pancreatic cancer, skin cancer, head and neck cancer, breast cancer, lung cancer, skin or intraocular malignant melanoma, kidney cancer, uterine cancer, ovarian cancer, colon cancer, rectal cancer, anal region cancer, colorectal cancer, stomach cancer, testicular cancer, fallopian tube cancer endometrial carcinoma, cervical carcinoma, vaginal carcinoma, vulvar cancer, non-Hodgkin's lymphoma, esophageal cancer, small intestinal cancer, endocrine system cancer, thyroid cancer, parathyroid cancer, adrenal gland cancer, soft tissue sarcoma, urethral cancer, penile cancer, childhood cancer, lymphocytic lymphoma, bladder cancer, ureter cancer, renal pelvic carcinoma, central nervous system (CNS) cancer, primary CNS lymphoma, tumor angiogenesis, spinal cancer, brainstem glioma, pituitary adenoma, Kaposi's sarcoma, epidermal cancer, squamous cell carcinoma, multiple myeloma, B-cell lymphoma, Hodgkin's lymphoma, acute myeloid lymphoma, chronic myeloid leukemia, chronic lymphocytic leukemia, follicular lymphoma, diffuse large B-cell lymphoma, Burkitt's lymphoma, immune large-cell lymphoma, progenitor B-lymphoblastic lymphoma, mantle cell lymphoma, acute lymphoblastic lymphoma, mycosis fungoides, anaplastic large-cell lymphoma, acute myeloid leukemia, acute lymphoblastic leukemia, hepatoblastoma, retinoblastoma, peritoneal cancer, brain tumor, thymic cancer, T-cell lymphoma or precursor T-lymphoblastic lymphoma, and any combination of the above cancers.

In some embodiments, a cancer or tumor being targeted by the subject invention is in any of a variety of stages including newly diagnosed, relapsed, refractory, progressive disease, remission, and others. In some embodiments, the cancer or tumor being treated is a newly diagnosed cancer. In some embodiments, the cancer or tumor is a recurrent cancer (e.g., a recurrent gynecologic cancer such as recurrent epithelial ovarian cancer, recurrent fallopian tube cancer, recurrent primary peritoneal cancer, or recurrent endometrial cancer). In some embodiments, the present invention is applicable to treatment of metastatic cancers.

In specific embodiments, a cancer or tumor being treated according to the subject invention is a breast cancer. In a specific embodiment, the breast cancer is TNBC.

As used herein, the term "subject" refers to an animal, such as a mammal, for example a human. The methods described herein can be useful in both human therapeutics and veterinary applications. In some embodiments, the subject is a mammal (including animal models of disease), and in some embodiments, the subject is human. Non-limiting examples of subjects include canine, porcine, rodent, feline, bovine, poultry, equine, human, and a non-human primate.

In one embodiment, in the method of treating cancer or a tumor, the subject may be treated with one or more additional therapeutic agents for treating cancer or a tumor before, during, and/or after administering to the subject an effective amount of an organoarsenical or a salt thereof. In another embodiment, in the method of treating cancer or a tumor, the subject is not treated with any additional therapeutic agents for treating cancer or a tumor before, during, and/or after administering to the subject an effective amount of an organoarsenical or a salt thereof.

As used herein, the term "treatment" or any grammatical variation thereof (e.g., treat, treating, treated, etc.) includes but is not limited to, the application or administration to a subject (or application or administration to a cell or tissue from a subject) with the purpose of delaying, slowing, stabilizing, curing, healing, alleviating, relieving, altering, remedying, less worsening, ameliorating, improving, or affecting the disease or condition, or the symptom of the disease or condition. The term "treating" refers to any indication of success in the treatment or amelioration of a pathology or condition, including any objective parameter such as abatement, remission, lessening of the rate of worsening, lessening severity of the disease, or diminishing of symptoms.

In certain embodiments, the organoarsenical or a salt thereof of the subject invention may be administered by inhalation, orally, intra-nasally, topically, intramuscularly, subcutaneously, intrathecally, intravenously or intraperitoneally by infusion or injection. In some embodiments, the hydrogel particles according to the present invention are administered orally, subcutaneously, intraperitoneally, or intravenously. The particular mode of administration and the dosage regimen will be selected by the attending clinician, taking into account the particulars of the case (e.g., the subject, the disease, the disease state involved). Treatment may involve daily or multi-daily doses of compound(s) over a period of a few days to months, or even years.

In some embodiments, a suitable dose of the organoarsenical or a salt thereof according to the present invention will be in the range of from about 0.001 to about 100 mg/kg of body weight per day, preferably from about 0.01 to about 100 mg/kg of body weight per day, more preferably, from about 0.1 to about 50 mg/kg of body weight per day, or even more preferred, in a range of from about 1 to about 10 mg/kg of body weight per day. For example, a suitable dose may be about 1 mg/kg, 10 mg/kg, or 50 mg/kg of body weight per day.

In some embodiments, the organoarsenical or a salt thereof according to the subject invention can be conveniently administered in unit dosage form, containing for example, about 0.05 to about 10000 mg, about 0.5 to about 10000 mg, about 5 to about 1000 mg, or about 50 to about 500 mg of the organoarsenical per unit dosage form.

The organoarsenical or a salt thereof according to the subject invention may conveniently be presented in a single dose or as divided doses administered at appropriate intervals, for example, as one dose per day or as two, three, four or more sub-doses per day. The sub-dose itself may be further divided, e.g., into a number of discrete loosely spaced administrations.

Optionally and as discussed herein, the method of treating cancer or a tumor in a subject according to the subject invention utilizes one or more additional therapeutic agents for treating cancer or a tumor to provide a combination therapy. The additional therapeutic agent(s) may be administered separately or otherwise formulated in the same composition as the organoarsenical or the salt thereof of the invention. In some embodiments, the additional therapeutic agent(s) are provided in a composition that is separate from the composition comprising the organoarsenical or a salt thereof of the present invention. Such separate composition is administered simultaneously with or at a time that is some time before or after the administration of the composition comprising the organoarsenical or a salt thereof of the present invention. In some embodiments, the additional therapeutic agent(s) are included in the compositions of the present invention within a therapeutically useful and effective concentration range, as determined by methods that are known in the medical and pharmaceutical arts. The concentration of any particular additional therapeutic agent may be in the same range as is typical for use of that agent as a monotherapy, or the concentration may be lower than a typical monotherapy concentration if there is synergy.

In other embodiments, the method of treating cancer or a tumor in a subject in need thereof according to the subject invention utilizes a composition comprising an effective amount of an organoarsenical or a salt thereof as the only active ingredient in the composition.

In one embodiment, the method of treating cancer or a tumor in a subject in need thereof according to the subject invention further comprises evaluating the activity of glutaminase, e.g., KGA in the cancer or tumor cells of the subject before, during, and/or after administering to a subject an effective amount of an organoarsenical or a salt thereof or a pharmaceutical composition comprising an organoarsenical or a salt thereof.

In one embodiment, the organoarsenical used herein is selected from, for example, trivalent organoarsenicals, pentavalent organoarsenicals, and salts thereof. In a specific embodiment, the trivalent organoarsenical is selected from, for example, the trivalent form of hydroxyarsinothricin (R-AST-OH), trivalent form of roxarsone (Rox(III)), and a salt thereof. In a specific embodiment, the pentavalent otganoarsenical is selected from, for example, the pentavalent form of thiolated hydroxyarsinothricin (T-AST-OH), pentavalent form of dithiolated hydroxyarsinothricin (DT-AST-OH), and a salt thereof.

In specific embodiments, evaluating the activity of glutaminase, e.g., KGA, of the subject may comprise obtaining/extracting cancerous or tumorous cells from the subject, and detecting the activity of glutaminase, e.g., KGA, within the cancerous or tumorous cells. According to the subject invention, detecting the activity of glutaminase, e.g., KGA, may be conducted by any known process in the art by determining the glutaminase, e.g., KGA, concentration, the glutamate concentration, and/or kinetics of glutaminase, e.g., KGA. In one embodiment, detecting the activity of glutaminase, e.g., KGA, is conducted by a glutaminase activity assay.

In one embodiment, the method of treating cancer or a tumor in a subject in need thereof according to the subject invention further comprises evaluating the activity of KGA of the subject before and after administering to the subject an effective amount of an organoarsenical or a salt thereof.

In specific embodiments, glutaminase, e.g., KGA, activity after administering to the subject an effective amount of an organoarsenical or a salt thereof decreases by at least 95%, at least 90%, at least 85%, at least 80%, at least 75%, at least 70%, at least 65%, at least 60%, at least 55%, at least 50%, at least 45%, at least 40%, at least 35%, at least 30%, at least 25%, at least 20%, at least 15%, or at least 10%, compared to the activity of glutaminase, e.g., KGA, before administering to the subject an effective amount of an organoarsenical or a salt thereof.

In one embodiment, the subject invention provides a method of treating cancer or a tumor, the method comprising administering to a subject in need thereof an effective amount of an organoarsenical or a salt thereof or a pharmaceutical composition of the subject invention, wherein the method further comprises forming one or more covalent bonds between glutaminase, e.g., KGA, of cancerous or tumorous cells of the subject and the organoarsenical or the salt thereof upon administering to the subject an effective amount of the organoarsenical or the salt thereof or the pharmaceutical composition of the subject invention, and/or evaluating the activity of glutaminase, e.g., KGA, of the subject before, during, and/or after administering to the subject an effective amount of the organoarsenical or the salt thereof or the pharmaceutical composition of the subject invention, wherein the organoarsenical is trivalent form of hydroxyarsinothricin (R-AST-OH), trivalent form of roxarsone (Rox(III)), pentavalent form of thiolated hydroxyarsinothricin (T-AST-OH), pentavalent form of dithiolated hydroxyarsinothricin (DT-AST-OH), or any combination thereof.

In one embodiment, the subject invention provides a method of treating breast cancer, the method comprising administering to a subject in need thereof an effective amount of an organoarsenical or a salt thereof, or a pharmaceutical composition of the subject invention.

In certain embodiments, the method may further comprise forming one or more covalent bonds between KGA of breast cancer cells of the subject and the organoarsenical or the salt thereof upon administering to the subject, and/or evaluating the activity of KGA before, during, and/or after administering to the subject an effective amount of the organoarsenical or the salt thereof, wherein the organoarsenical is trivalent form of R-AST-OH, trivalent form of Rox(III), pentavalent form of T-AST-OH, pentavalent form of DT-AST-OH, or any combination thereof.

In one embodiment, the subject invention provides a method of treating TNBC, the method comprising administering to a subject in need thereof an effective amount of an organoarsenical of the subject invention or a salt thereof, or a pharmaceutical composition of the subject invention.

In certain embodiments, the method may further comprise forming one or more covalent bonds between KGA of TNBC cells of the subject and the organoarsenical or the salt thereof upon administering to the subject an effective amount of the organoarsenical or the salt thereof, and/or evaluating the activity of KGA of the subject before, during, and/or after administering to the subject an effective amount of the organoarsenical or the salt thereof, wherein the organoarsenical is R-AST-OH, Rox(III), T-AST-OH, DT-AST-OH, or any combination thereof.

In one embodiment, the subject invention provides a method of inhibiting the interaction between glutamine and glutaminase (e.g., KGA) by using the compounds or compositions of the subject invention. In one embodiment, the subject invention also provides a method of inhibiting/reducing/suppressing the conversion of glutamine to glutamate by using the compounds or compositions of the subject invention.

In one embodiment, the subject invention provides a kit comprising, in one or more containers, a compound, or composition of the present invention. In one embodiment, the subject invention provides a kit contains an organoarsenical or a salt thereof. In specific embodiments, the kit comprises at least one of R-AST-OH, Rox(III), T-AST-OH, and DT-AST-OH. In one embodiment, the kit is for use in inhibiting catalytic activity of glutaminase, e.g., KGA or for treating cancer.

In some embodiments, the compounds described herein may be assembled into pharmaceutical or diagnostic or research kits to facilitate their use in therapeutic, diagnostic or research applications. Specifically, such kits may include one or more compounds described herein, along with instructions describing the intended therapeutic application and the proper administration of these compounds. In certain embodiments, compounds in a kit may be in a pharmaceutical formulation and dosage suitable for a particular application and for a method of administration of the compounds.

As used herein, the singular forms "a", "an", and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", and "comprise" can be used interchangeably; "consisting essentially of", and "consists essentially of" can be used interchangeably; and "consisting", and "consists" can be used interchangeably.

When ranges are used herein, such as for dose ranges, combinations and subcombinations of ranges (e.g., subranges within the disclosed range), specific embodiments therein are intended to be explicitly included.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of concentrations of ingredients where the term "about" is used, these values include a variation (error range) of 0-10% around the value (X±10%).

In the present disclosure, ranges are stated in shorthand to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. Values having at least two significant digits within a range are envisioned, for example, a range of 5-10 indicates all the values between 5.0 and 10.0 as well as between 5.00 and 10.00 including the terminal values. When ranges are used herein, combinations and subcombinations of ranges (e.g., subranges within the disclosed range) and specific embodiments therein are explicitly included.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

EXAMPLES

Materials and Methods

Reagents

All chemicals and enzymes were purchased from Sigma-Aldrich Co, LLC (St. Louis, MO, USA), unless otherwise stated. AST-OH was chemically synthesized as described by Suzol et al. (Suzol et al.; Yoshinaga, M. Semisynthesis of the organoarsenical antibiotic arsinothricin. *J. Nat. Prod* 2020, 83, 2809-2813). Chemically synthesized AST-OH is racemic mixture, and we consider only L-form in all studies mentioned in the subject invention. AST-OH is authenticated by high pressure liquid chromatography (series 2000, Perkin-Elmer) (HPCL) coupled to inductively coupled plasma mass spectrometry (ELAN DRC-e; Perkin-Elmer, Waltham, MA, USA) (ICP-MS) before use. Trivalent R-AST-OH and Rox (III) were prepared by chemical reduction of the arsenic atom in pentavalent AST-OH and Rox(V) (FIG. 3).

Purification of Recombinant KGA

The kidney isoform of human glutaminase (KGA) consists of 669 amino acid residues. The gene for KGA without the mitochondrial localization sequence (residues 72 to 598) was chemically synthesized by GenScript USA Inc. (New Jersey) with codon optimization for expression in *E. coli*. The synthetic gene was inserted into vector plasmid pET28a (+). The resulting plasmid containing the KGA gene with the sequence for a six-histidine tag at the 3'-end and under control of the T7 promoter. The plasmid was transformed into *E. coli* Rosetta (DE3) cells for protein expression. Cells of *E. coli* Rosetta (DE3) bearing pET28a(+)-KGA were grown in lysogeny broth (LB) medium with shaking at 37° C. At an $A_{600\ nm}$ of 0.5-0.6, 0.1 mM isopropyl 1-thio-β-D-galactopyranoside (IPTG) was added and growth continued at 16° C. for 20 h. The cells were harvested by centrifugation and suspended in buffer A (50 mM MOPS, 20 mM imidazole, pH 7.5, 0.5 M NaCl and 20% glycerol). The cells were lysed by a one-time passage through a French pressure cell at 20,000 psi and immediately mixed with 2.5 µl per g of wet cells of the protease inhibitor diisopropylfluorophosphate. The cell lysate was centrifuged at 35,000 rpm using a T865 rotor (Thermo Fisher Scientific, Waltham, MA, USA) for 60 min at 4° C. The supernatant solution was applied onto a Ni-NTA column (QIAGEN Sciences, Hilden, Germany) at a flow rate of 1.5 ml/min and washed with 20 column volumes (100 ml) of buffer A. Bound protein was eluted with buffer A containing 0.2 M imidazole. Fractions containing the protein were pooled and concentrated using a 30 kDa Amicon Ultra centrifugal filter (EMD Millipore, Billerica, MA, USA). The concentrated protein was rapidly frozen and stored at −80° C. until use.

Cell Culture

TNBC cell lines MDA-MB-231 (CRM-HTB-26™), HCC1569 (CRL-2330™) and the non-tumorigenic mammary epithelial cell line MCF12A (CRL-10782™) were purchased from the American Type Culture Collection (ATCC) (Manassas, VA, USA) and used to test anti-cancer effect/cell toxicity of arsenic compounds. All cell lines were cultured in the respective media suggested by the vendors in a 5% $CO_2$ humidified incubator at 37° C.

Example 1—KGA Activity Inhibition Assay

KGA Inhibition by AST-OH, AP4, and DON

Figure 4D:
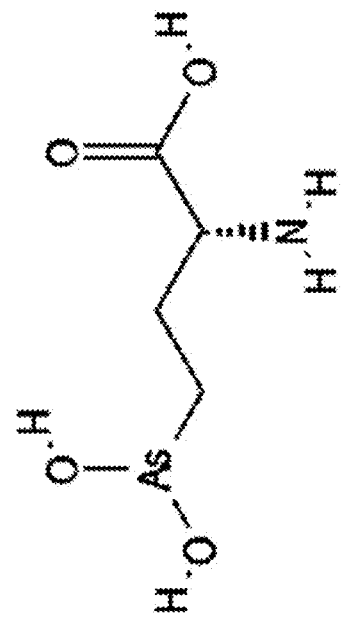
Figure 4E:
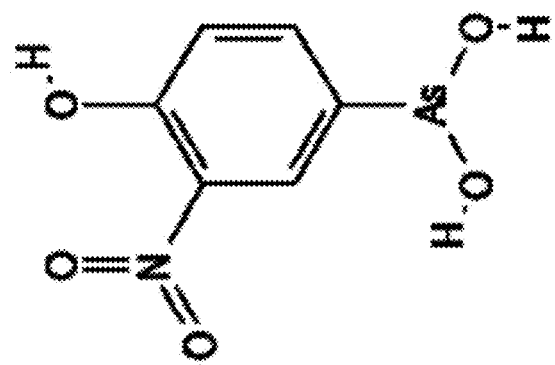
Figure 4C:
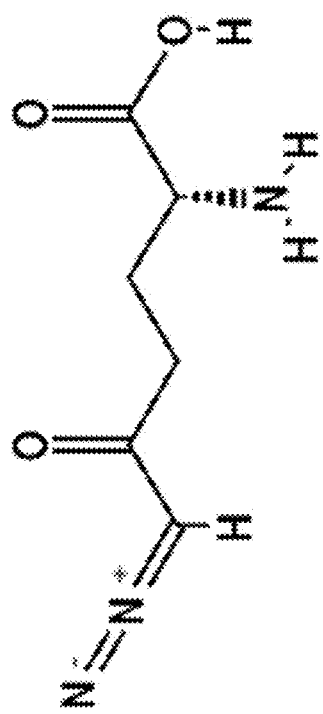

Inhibition of KGA catalytic activity was assayed spectrophotometrically using purified recombinant KGA with AST-OH, the structurally similar phosphonate AP4 and the well-known KGA inhibitor DON (FIGS. 4A-4C). Briefly, the catalytic activity of KGA was determined by measuring the production of NADH from the increase in absorption of at 340 nm at 37° C. for 30 min in a buffer containing 50 mM Tris-acetate (pH 8.6), 150 mM $K_2HPO_4$, 0.1 mg/ml bovine serum albumin (BSA), 0.25 mM EDTA, 1 mM DTT, 4 mM NAD+, 5 mM glutamine and 1 unit of glutamine dehydrogenase. The reaction was initiated by addition of glutamine.

Figure 5A:
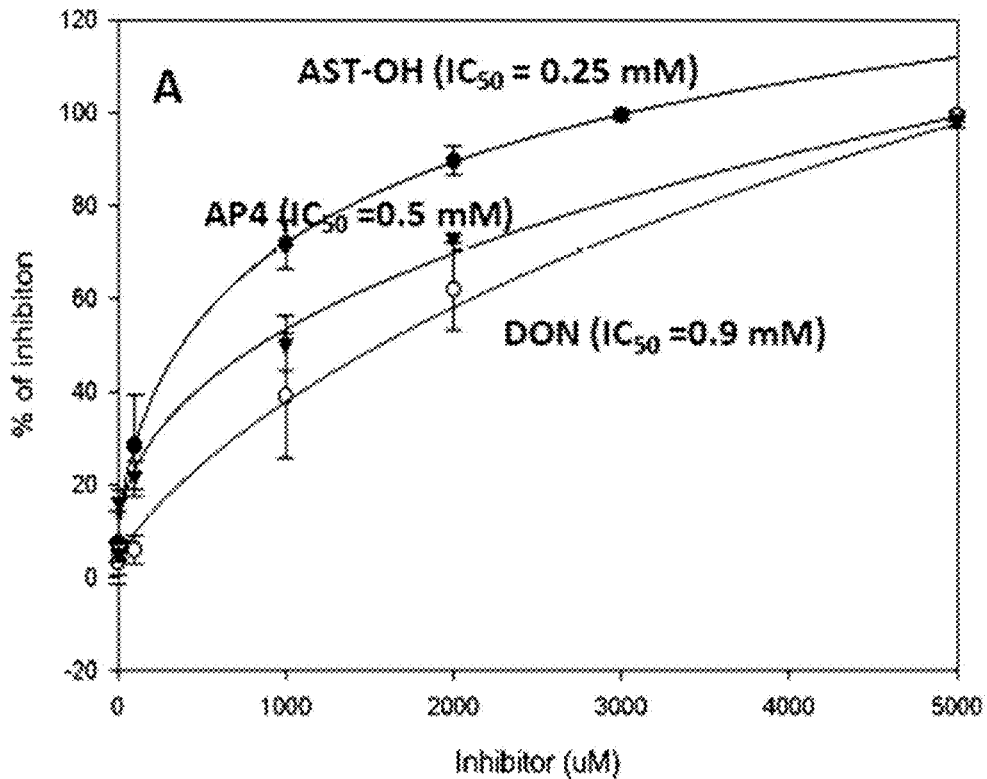
FIGS. 5A-5B. Assays of KGA inhibition: (5A) Spectroscopic assay with AST-OH, AP4 and DON; and (5B) luminescent assay with R-AST-OH and Rox(III).

The results showed that AST-OH and AP4 are better inhibitors than the competitive inhibitor DON, but none is particularly effective, with the half-maximal inhibitory concentration ($IC_{50}$) values in the submillimolar range (FIG. 5A).

KGA Inhibition by AST-OH and Rox(III)

Inhibition of KGA catalytic activity by trivalent organoarsenicals, including R-AST-OH and the trivalent reduced form of the aromatic arsenical roxarsone Rox(III), was determined using a Glutamine/Glutamate-GLO™ Assay Kit (Promega, Madison, WI, USA), which is a luminescent assay for detection of glutamate. The reducing agent used for the preparation of R-AST-OH and Rox(III) did not affect the assay. For assaying inhibition of KGA by trivalent organoarsenicals, KGA was preincubated with R-AST-OH or trivalent Rox(III) for 15 min, and the enzymatic reaction was initiated by addition of the substrate glutamine. The glutamate produced by KGA activity was assayed with the Glutamine/glutamate-GLO™ Assay kit. The effect of those inhibitors was compared from the half-maximal inhibitory concentration ($IC_{50}$) of each compound. $IC_{50}$ values were calculated by fitted regression using Sigma Plot (Inpixon, Palo Alto, CA).

Figure 5B:
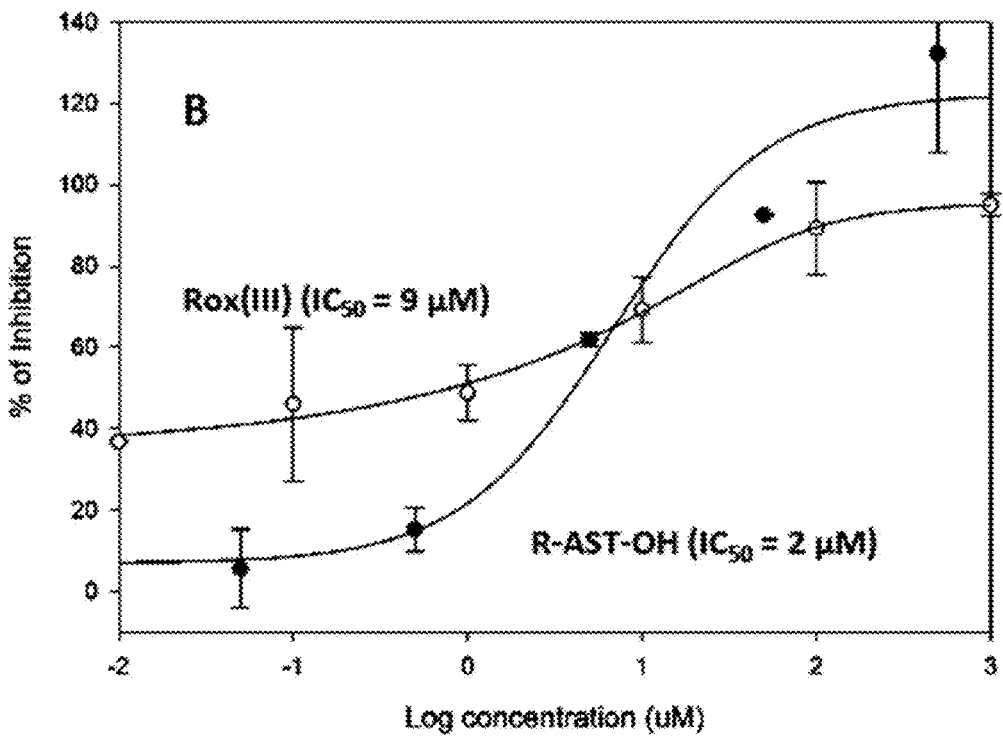

The calculated $IC_{50}$ value of 2 μM shows that R-AST-OH is a 125-fold more effective inhibitor of KGA than pentavalent AST-OH and 4.5-fold more effective than Rox(III) (FIG. 5B). R-AST-OH and Rox(III) also exhibited stronger inhibitory effects on the glutaminase enzyme than the competitive inhibitor, DON (FIGS. 5A-5B).

Example 2—KGA Binding Affinity Assay

The real time binding affinity of R-AST-OH and Rox(III) with purified KGA was determined using Isothermal Titration calorimetry (ITC). Binding assays were carried out using a MicroCal iTC200 (GE Healthcare Bio Sciences, Piscataway, NJ) with protein concentrations between 50 and 100 μM and inhibitor concentrations from 0.5 to 1 mM. Data were collected at 20° C. with 20 injections at 10 min intervals with a stirring speed of 1000 rpm. Spectra were analyzed using Origin 7.0 software (TA Instruments, New Castle, DE), and stoichiometry (n), binding constants ($K_d$) and enthalpy (ΔH (kcal/mol)) were calculated with a one site binding model.

Figure 6A:
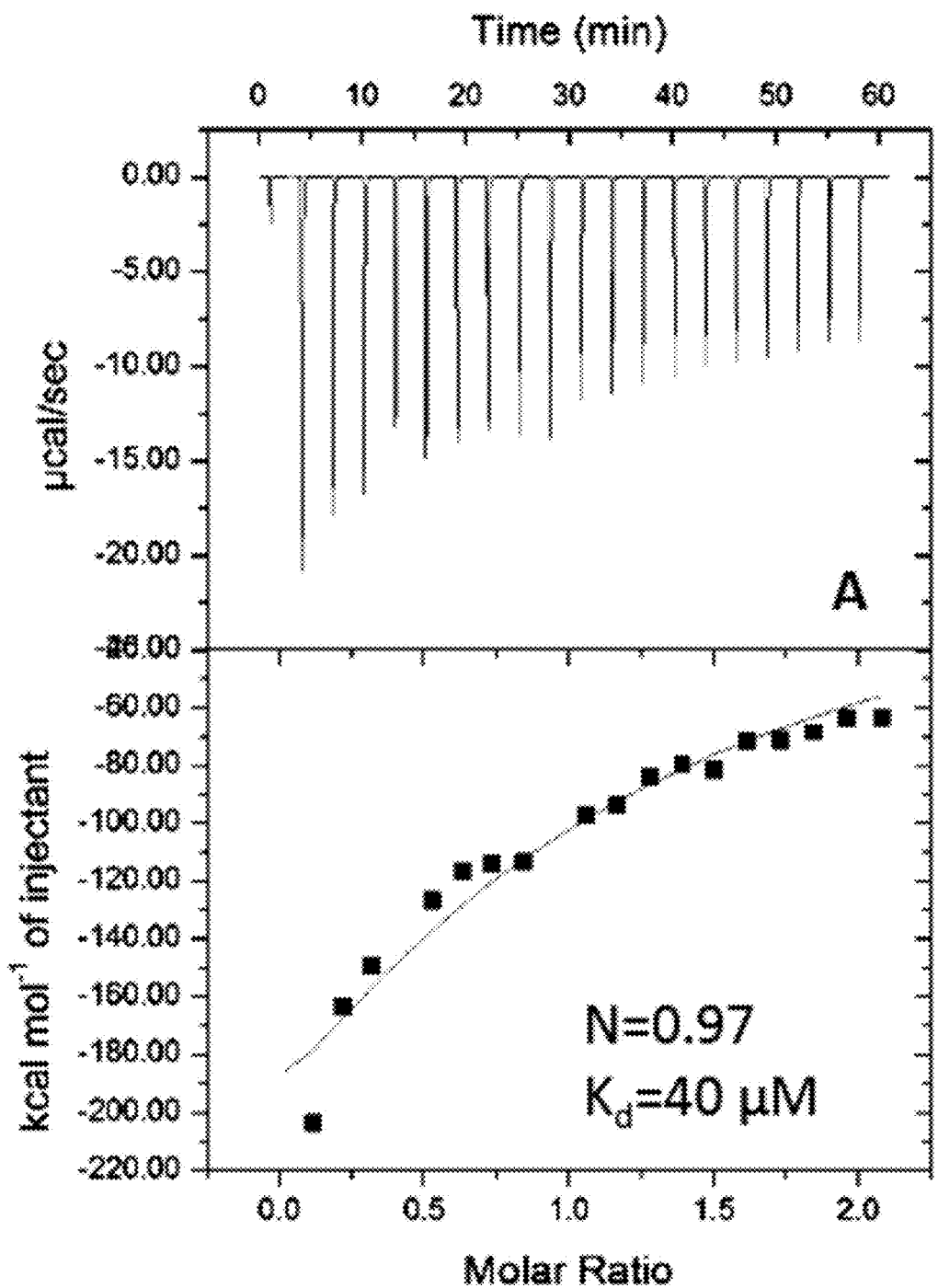
FIGS. 6A-6B. Isothermal calorimetry (ITC) analysis of (6A) R-AST-OH and (6B) Rox(III) binding to KGA.
Figure 6B:
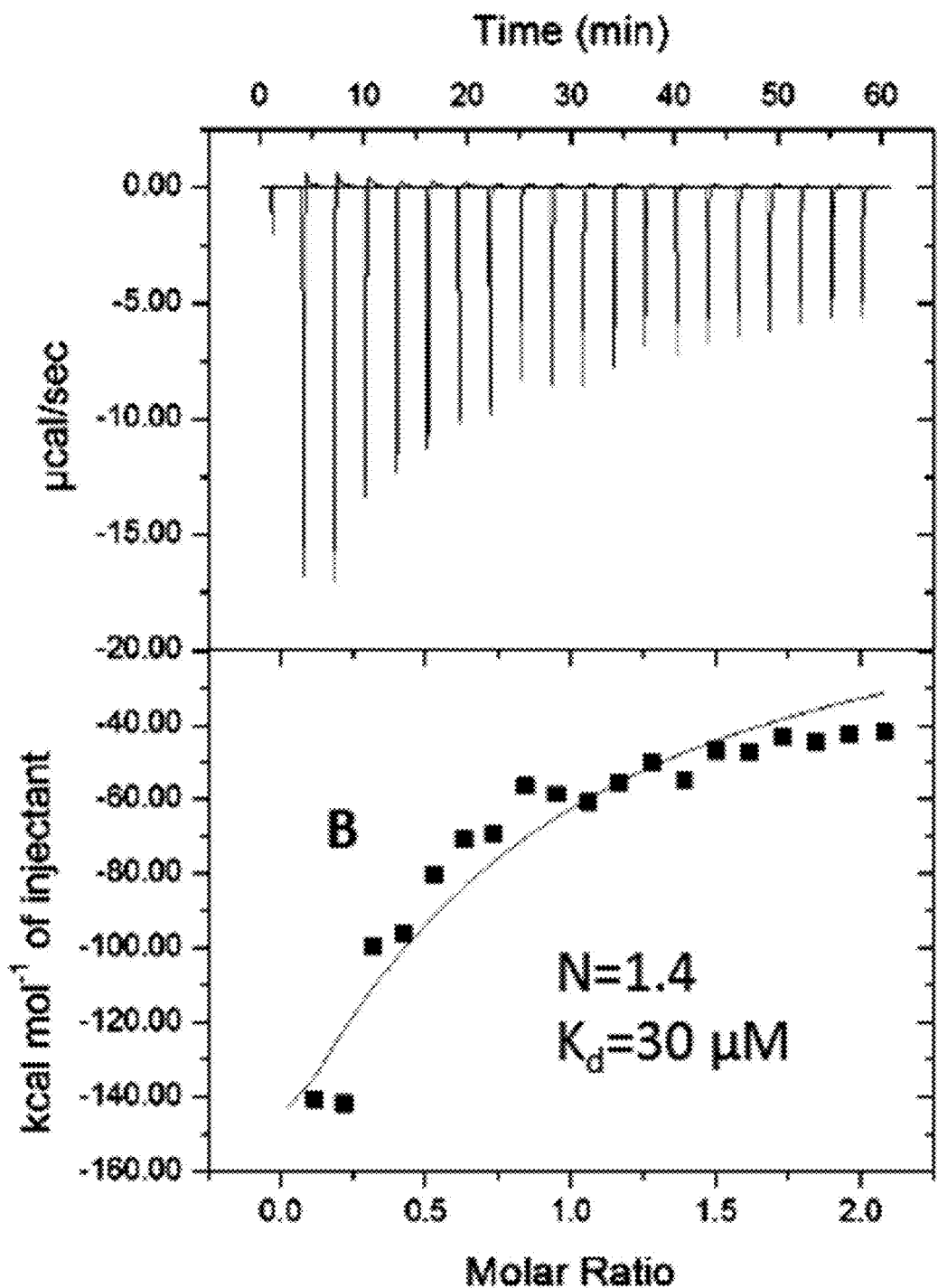

The apparent binding affinity ($K_d$) was 40 μM and 30 μM for R-AST-OH and Rox(III), respectively (FIGS. 6A-6B). Although this appears higher compared with the $IC_{50}$ values of these compounds as determined spectrophotometrically, it is likely because trivalent arsenicals bind slowly to the enzyme by forming an irreversible covalent bond, which is the optimum type of inhibition, since the spectrophotometric assay reflects slow binding kinetics, while the ITC results reflect the thermodynamics, which predominates in irreversible inhibition.

Example 3—Anti-Cancer Effect/Cell Toxicity Assay

Cancer Cell Toxicity of AST-OH, AP4, and DON

Figure 7A:
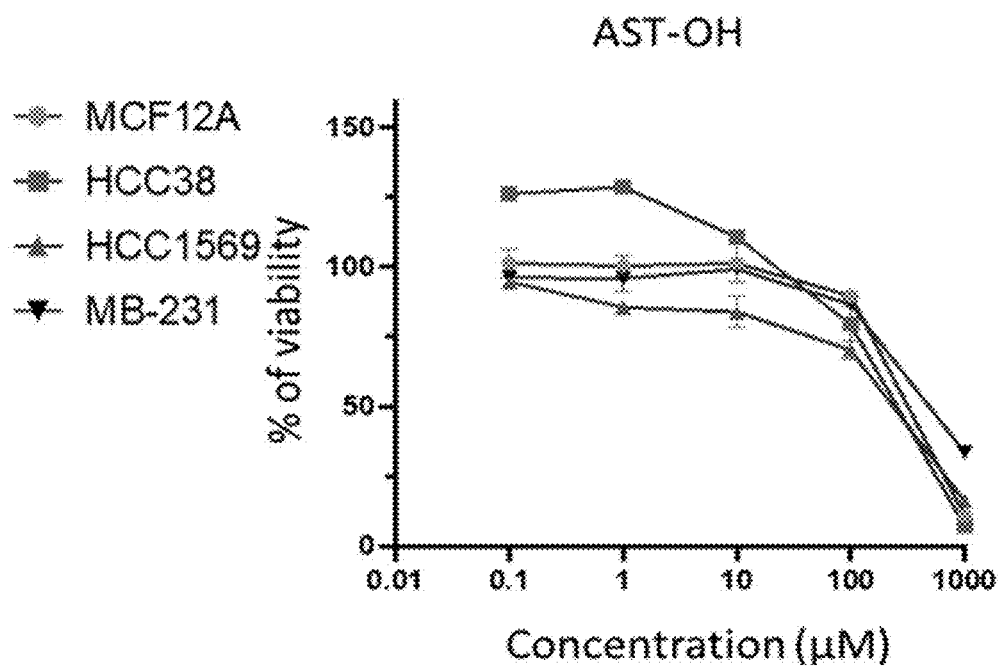
FIGS. 7A-7C. TNBC cell-based assay for pentavalent (7A) AST-OH, (7B) AP4 and (7C) DON.
Figure 7B:
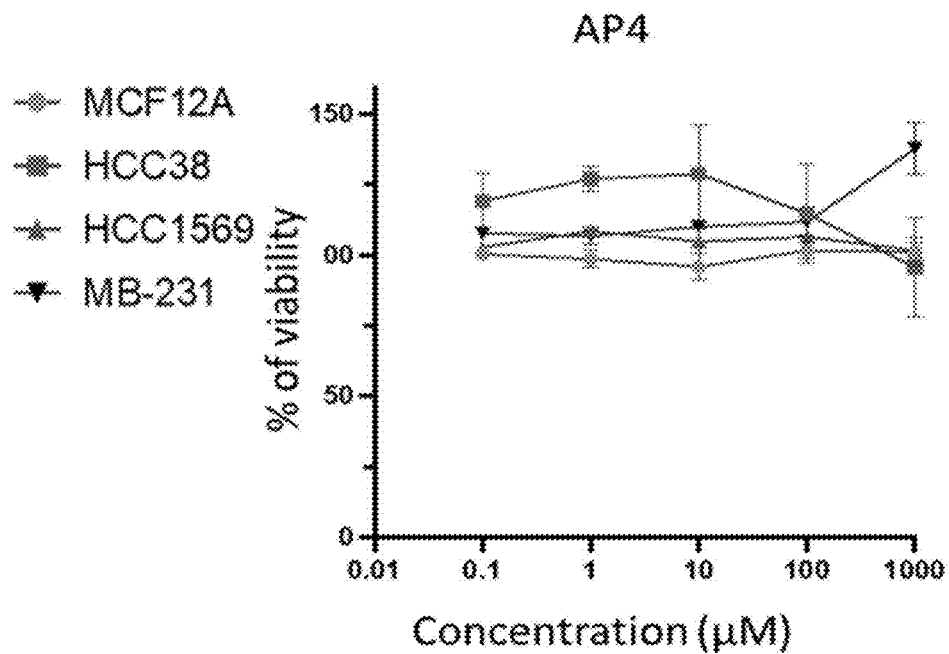
Figure 7C:
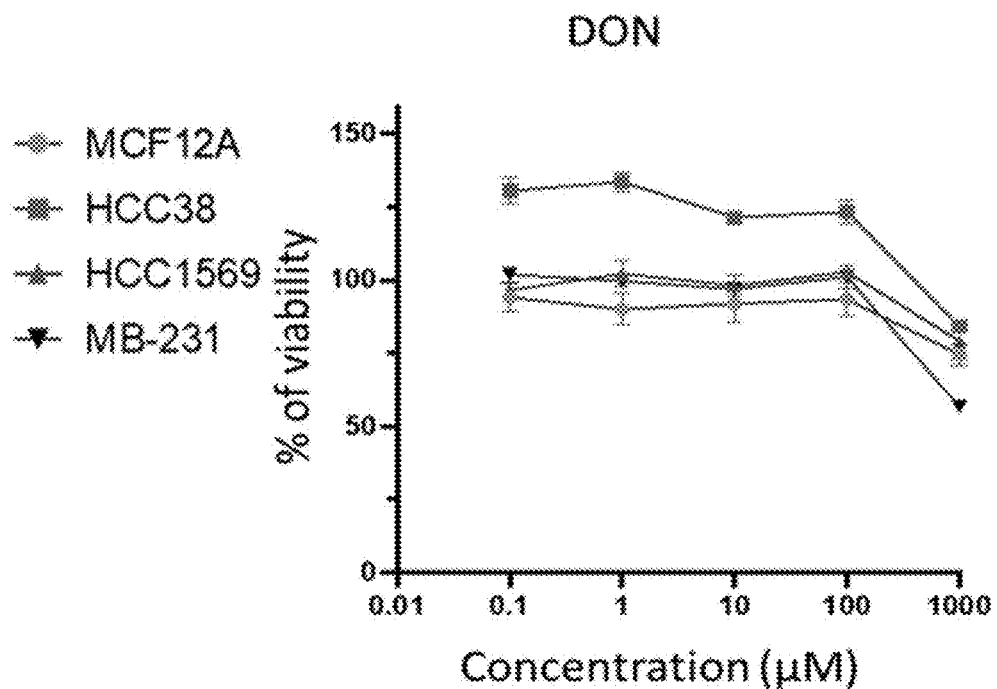

Cell viability was measured using an MTT (3-(4,5-dimethylthiazol-2-yl)-2,5-diphenyltetrazolium bromide) assay on cell lines MDA-MB-231, HCC1569, HCC38 and MCF12A (FIGS. 7A-7C).
Cancer Cell Toxicity of R-AST-OH and Rox(III)

To examine whether either R-AST-OH or Rox(III) inhibit growth of cancer cells, cell viability assays were conducted with TNBC cancer cell lines MDA-MB-231 (basal B subtype) and HCC1569 (basal A subtype). The effect of the trivalent organoarsenicals was compared with the FDA approved anti-cancer drug, Trisenox (ATO), an inorganic trivalent arsenical. The cytotoxicity of those compounds was also examined using normal breast cells (non-tumorigenic human breast epithelial cells) MCF12A.

All cell lines were seeded at a density of $3.0 \times 10^4$ cells/well in 96-well plates. After 24 h, the cells were further cultured in the presence or absence of the indicated concentrations of arsenic compounds for another 72 h, following which viability was determined using a CellTiter-Glo® Luminescent Cell Viability Assay (Promega).

Figure 8A:
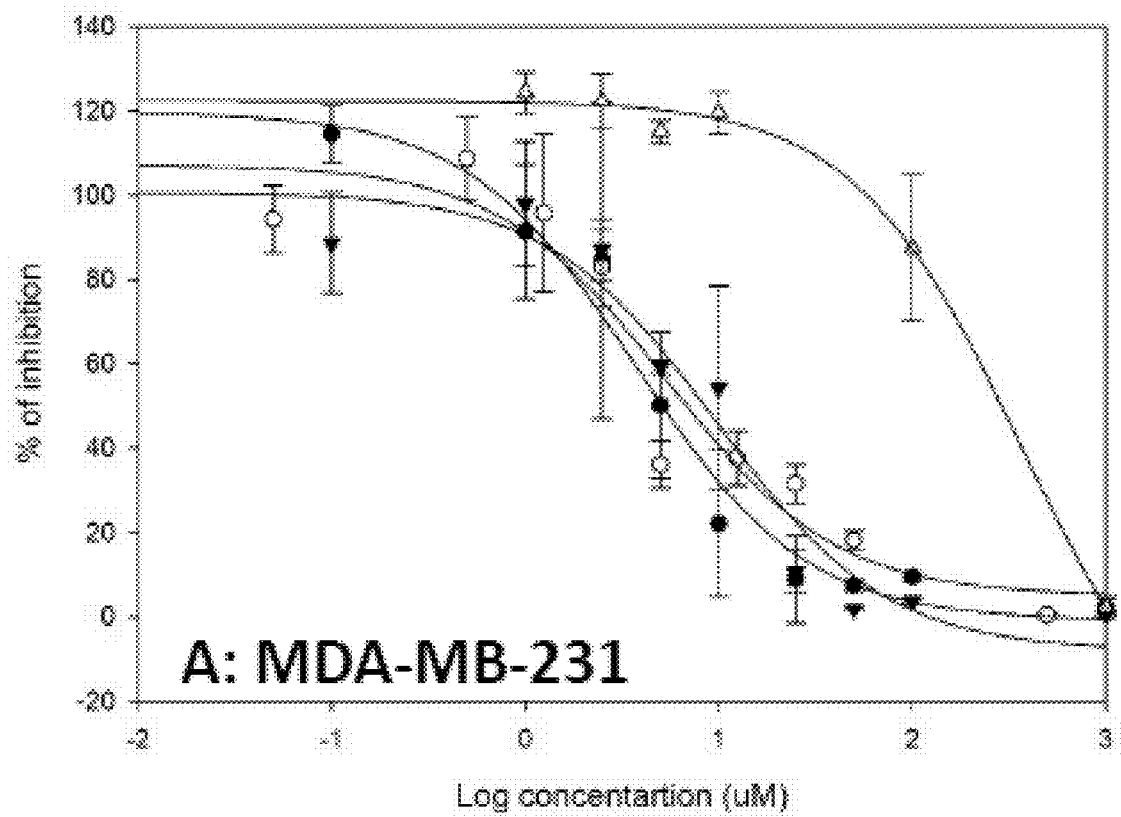
FIGS. 8A-8C. Antiproliferative activity in triple negative breast cancer cell lines (8A) MDA-MB-231, (8B) HCC1569, and (8C) the normal breast epithelial cell line MCF12A with R-AST-OH (○), Rox(III) (▼), ATO (●) or reducing agent alone (△).
Figure 8B:
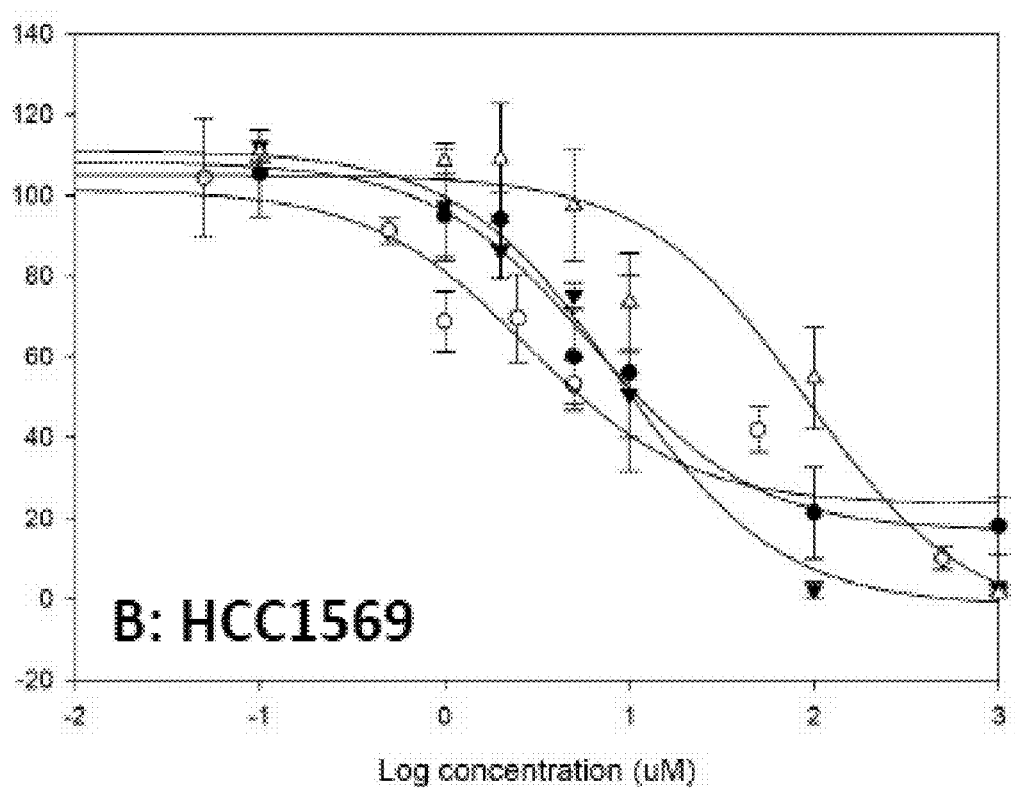
Figure 8C:
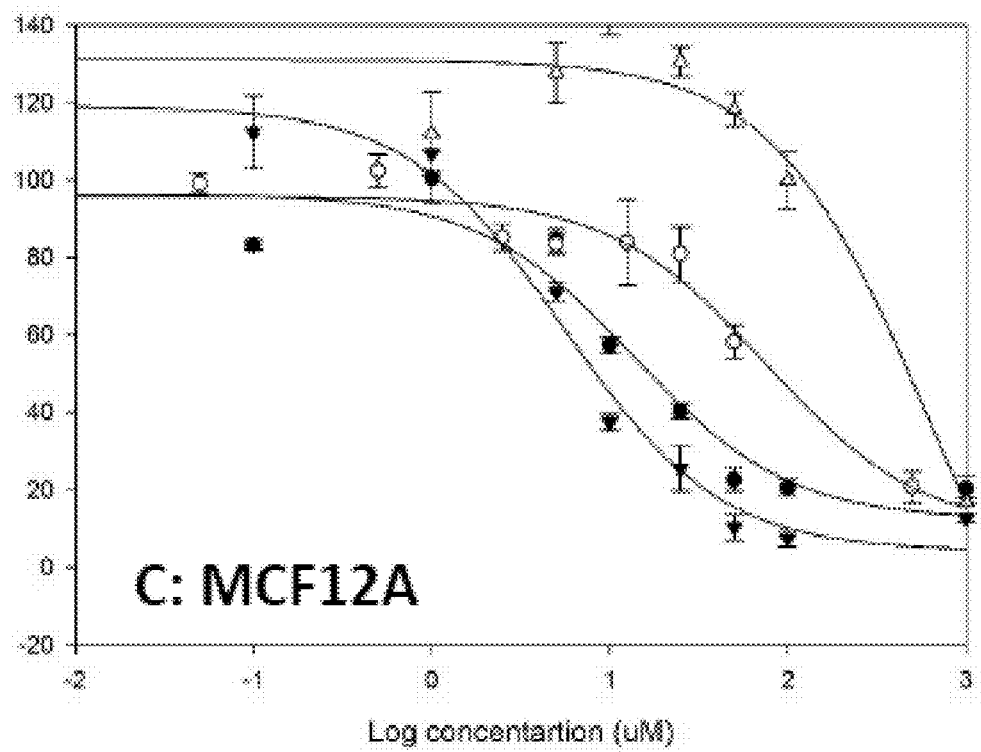

Results showed that at 10 μM R-AST-OH, approximately 64% of MDA-MB-231 cells and 47% of HCC1569 cells lost viability (FIGS. 8A-8C). The $IC_{50}$ for R-AST-OH can be inferred to be 3 and 5 μM for HCC1569 and MDA-MB-231 cells, respectively. The $IC_{50}$ for Rox(III) is 9 and 10 UM for HCC1569 and MDA-MB-231 cells, respectively, and for ATO is 6 and 4 μM for HCC1569 and MDA-MB-231 cells, respectively. $IC_{50}$ values for R-AST-OH, ATO, and Rox(III) with MCF12A cells were 75.0, 13.6, 5.6 μM, respectively, indicating that R-AST-OH has the least toxicity to normal cells among tested compounds. Overall R-AST-OH has more effective anti-cancer activity than Rox(III) in both cancer cell lines.

In this assay, both R-AST-OH and Rox(III) produced significant loss of viability in both TNBC cancer cell lines MDA-MB-231 and HCC1569, suggesting that both would have anticancer effects, comparing R-AST-OH and Rox(III) with the well-known anticancer drug ATO, both were more cyotoxic to growth of MDA-MB-231 and HCC1569 cells than ATO, indicating that R-AST-OH is a more effective therapeutic agent than ATO. In addition, viability assays with the normal breast cell line MCF12A cells demonstrated that R-AST-OH exhibits the lowest toxicity, indicating that it could be a good lead compound for treatment of breast cancer.

Comparison between AST-OH and R-AST-OH further indicates that the trivalent R-AST-OH (FIGS. 8A-8B) has more effective anti-cancer activity in both cancer cell lines than the pentavalent AST-OH (FIG. 7A).

Example 4—Arsenic Uptake Assay

MDA-MB-231 cells were seeded at a density of $1.0 \times 10^5$ cells/well in 6-well plates. After 24 h, the cells were further cultured with or without 5 μM of arsenic compounds for another 72 h. Cells were rinsed with PBS four times followed by collecting pellets. For measurement of cellular uptake, the dried cells were digested with 70% nitric acid (≥99.999% trace metals basis) at 70° C. for 60 min, allowed to cool to room temperature and diluted to a final concentration of 2% nitric acid with HPLC-grade water, and the total arsenic content of each sample was quantified using ICP-MS.

Figure 9:
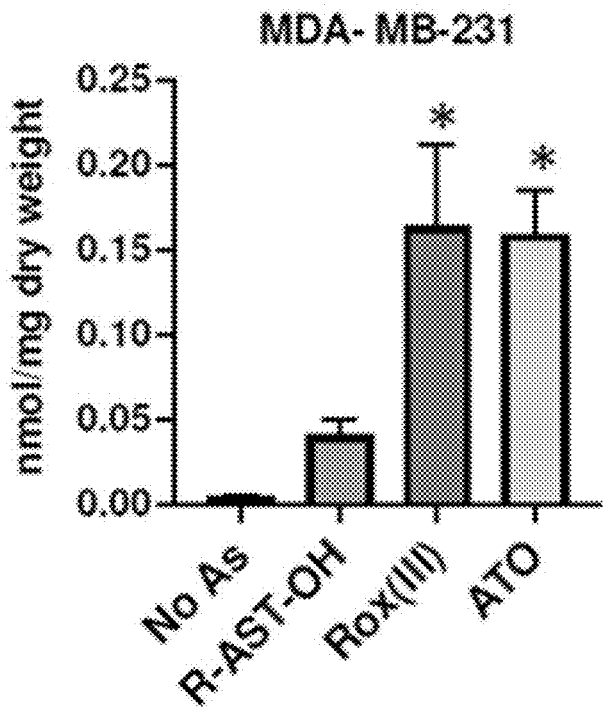
FIG. 9. Permeability of arsenic compounds was measured using MDA-MB-231 cells. The significance of uptake is analyzed by one-way ANOVA test: *$p<0.05$ (N=3). Shown is the average, with SEM as error bars.

Cell permeability assays with MDA-MB-231 cells showed differential uptake of arsenicals, where ATO has the highest permeability, and R-AST-OH has the lowest permeability (FIG. 9). The result that ATO and Rox(III) have better permeability than R-AST-OH suggested that, even with lower uptake, R-AST-OH is still more effective than the other trivalent arsenicals. R-AST-OH may show significantly more potent anti-cancer efficacy through chemical modification to produce more permeable derivatives.

In summary, the novel organoarsenical R-AST-OH is more cytotoxic toward breast cancer cells than the inorganic arsenical ATO, which is a proven drug for treatment of soft tissue malignancies. The results suggest that R-AST-OH may be an effective chemotherapeutic agent for breast cancer.

Example 5—In Silico Docking of KGA with R-AST-OH and Rox(III)

The binding mode of R-AST-OH and Rox(III) with KGA was analyzed by in silico docking using AUTODOCK4. The three dimensional structure of R-AST-OH and Rox(III) was generated using the Molview server. Both molecules were docked with the crystal structure of KGA (PDB ID: 4O7D) using AutoDock4 in AutoDockTools. The grid center was positioned on the DON binding site of KGA with a size of 40 Å×40 Å×40 Å. The other docking parameters were set as default values. The top ranked confirmation was select for further analysis. The binding energy of the complex of KGA-R-AST-OH and KGA-Rox(III) are −4.27 and −4.89 kcal/mol, respectively. The molecular graphics were performed using PyMol.

Figure 10A:
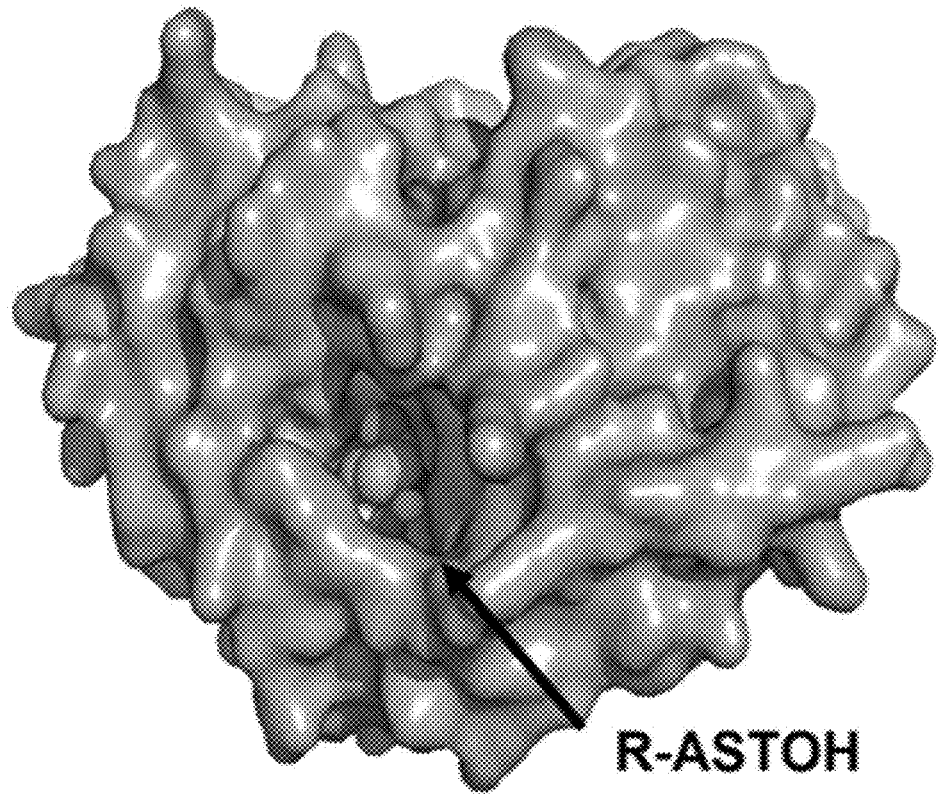
FIGS. 10A-10C. In silico docking of (10A, 10B) R-AST-OH and (10C) Rox(III) with KGA. Arsenicals are shown as green sticks.
Figure 10B:
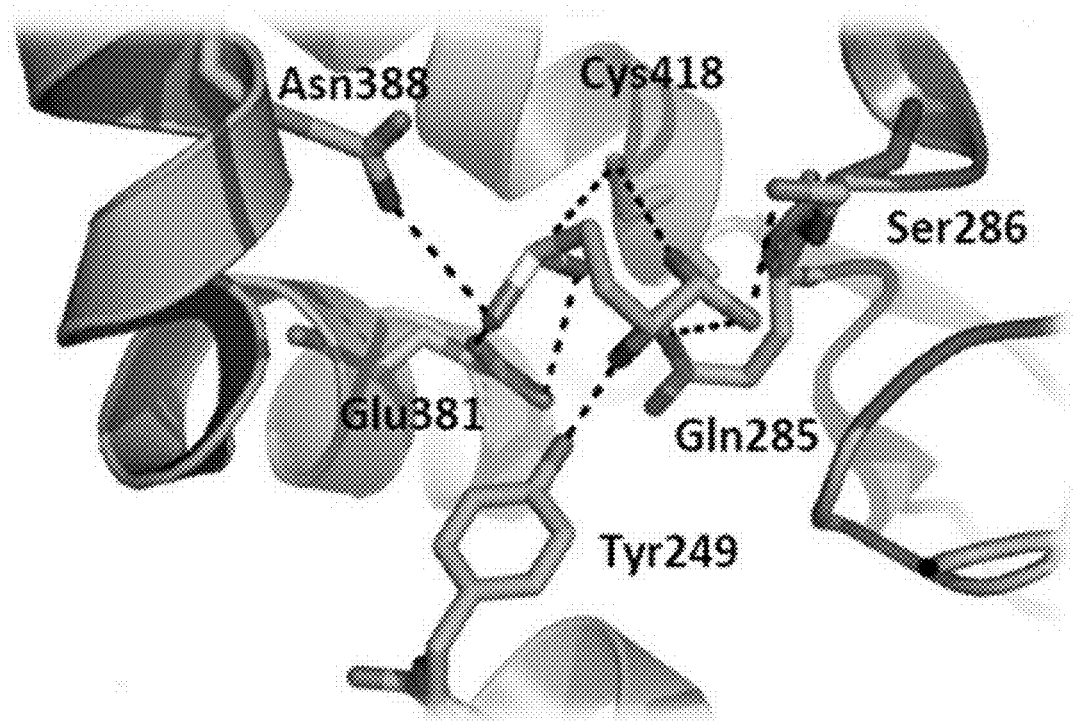
Figure 10C:
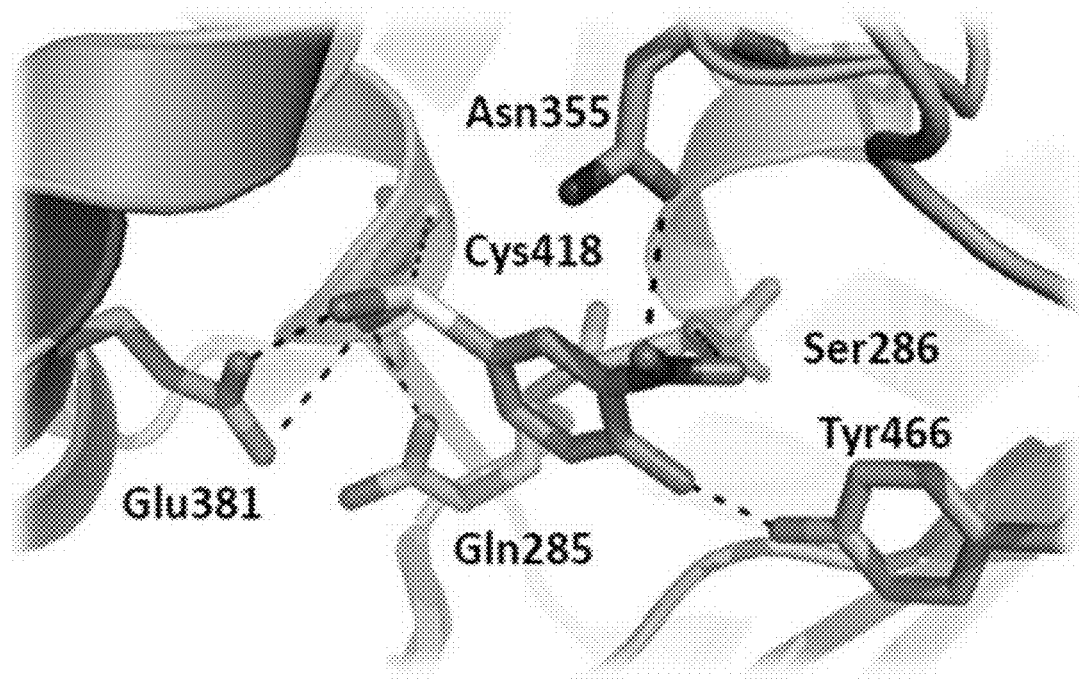

The results showed that both inhibitors R-AST-OH and Rox(III) fit well into the catalytic site. The arsenical moiety of R-AST-OH is surrounded by KGA residues Asn388, Glu381 and Cys418 (FIG. 10B). The distance between the arsenic and the sulfur atoms of Cys418 is predicted to be 3.9 Å, indicating a covalent bond. The carboxylate group of R-AST-OH interacts with the catalytic residue Ser286. Similarly, the arsenical moiety of Rox (III) is surrounded by Glu381 and Cys418. The nitro group of Rox(III) interacts with Ser286. The arsenic atom of Rox(III) is close to sulfur atom of Cys418, at a distance of 3.6 Å. In general, trivalent arsenic and sulfur have high affinity for each other and will form a covalent bond at this distance, indicating that R-AST-OH and Rox(III) should be an irreversible covalent inhibitors of KGA.

The results of Examples 1-5 showed that the trivalent arsenicals R-AST-OH and Rox (III) exhibit a stronger inhibitory effect on glutaminase than the well-characterize competitive inhibitor DON. The binding affinity of R-AST-OH and Rox(III) measured by ITC is higher than the $IC_{50}$ value of those compounds determined by spectrophotometrically. It's believed that the spectrophometic assay reflects slow binding kinetics, while the ITC results reflect the thermodynamics, which predominate in irreversible inhibition. The results of the docking analysis indicate that the distance between the arsenic atom and the sulfur atom of cysteine is short enough to create a covalent bond between them. Covalent bond formation would essentially result in irreversible inhibition, consistent with the higher binding affinity found by ITC. TNBC-cell-based assays using MDA-MB-231 and HCC1569 cell lines showed that R-AST-OH kills TNBC cells and is not cytotoxic to control non-TNBC cell line. The results show that R-AST-OH is a single warhead for KGA by irreversibly binding to KGA through formation of an As—S bond, and thus is a promising lead compound for the design of new drugs for treatment of TNBC.

Example 6—Thiolated Pentavalent Organoarsenicals and Activities Thereof

Figure 11A:
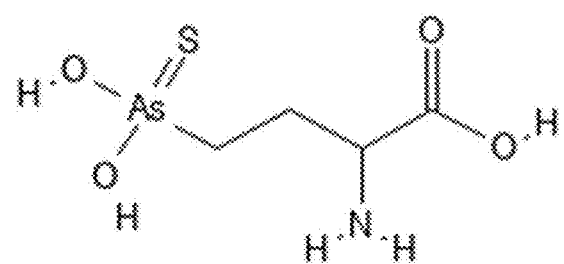
FIGS. 11A-11B. Chemical structures: (11A) thiolated pentavalent organoarsenical (T-AST-OH); (11B) dithiolated pentavalent organoarsenical (DT-AST-OH).
Figure 11B:
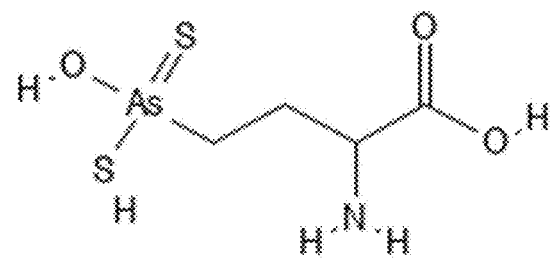

Thiolated T-AST-OH (FIG. 11A) and dithiolated DT-AST-OH (FIG. 11B) are synthesized by a protocol of synthesis for dimethyl-mono-thiolated arsenate and dimethyl-di-thiolated arsenate. The synthesized compounds are validated by NMR spectroscopy.

Thiolated arsenicals are considerably more toxic than their oxygen-containing forms. In general, pentavalent arsenicals do not form covalent bonds with the sulfur atom of cysteines in proteins. In contrast, sulfide-activated pentavalent arsenic can bind to the sulfur atom of proteins with high affinity. Docking of R-AST-OH with KGA (FIG. 10B) shows that the As—OH bond is close to Cys418. Results show that changing As—OH and As═O to thiolated T-AST-OH and dithiolated DT-AST-OH can greatly increase the inhibitory efficacy of pentavalent AST-OH, and that T-AST-OH and DT-AST-OH can inhibit KGA with much higher affinity than AST-OH.

All patents, patent applications, provisional applications, and publications referred to or cited herein are incorporated by reference in their entirety, including all figures and tables, to the extent they are not inconsistent with the explicit teachings of this specification. It should be understood that the examples and embodiments described herein are for illustrative purposes only and that various modifications or changes in light thereof will be suggested to persons skilled in the art and are to be included within the spirit and purview of this application and the scope of the appended claims. These examples should not be construed as limiting. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

We claim:

1. A method of inhibiting kidney-type glutaminase (KGA) activity in a cell that expresses KGA, comprising contacting the cell with a trivalent organoarsenical, or a salt thereof, wherein the trivalent organoarsenical is trivalent hydroxyarsinothricin or trivalent roxarsone.

2. The method of claim 1, the cell being a cancer cell.

3. The method of claim 2, the cancer cell being a breast cancer cell.

4. The method of claim 3, the breast cancer cell being a TNBC cell.

5. A method of treating triple-negative breast cancer (TNBC), the method comprising administering to a subject having TNBC an effective amount of a composition comprising a trivalent organoarsenical, and a pharmaceutically-acceptable carrier, the trivalent organoarsenical being trivalent hydroxyarsinothricin or trivalent roxarsone.

6. The method of claim 5, the administration being through a local, oral, nasal, topical, intratumoural, transdermal, intra-articular, intravenous, intraperitoneal, intradermal, subcutaneous, or intramuscular route.

7. The method of claim 5, further comprising evaluating the catalytic activity of KGA in TNBC cells of the subject.

8. A method of disrupting and/or inhibiting growth and proliferation of TNBC cells, the method comprising administering to a subject having TNBC an effective amount of a trivalent organoarsenical, the trivalent organoarsenical being trivalent hydroxyarsinothricin or trivalent roxarsone.

9. The method of claim 8, further comprising detecting the catalytic activity of KGA in TNBC cells of the subject.

* * * * *